(12) United States Patent
Kakuta et al.

(10) Patent No.: US 7,825,250 B2
(45) Date of Patent: Nov. 2, 2010

(54) BINUCLEAR METAL COMPLEX, METAL COMPLEX DYE, PHOTOELECTRIC CONVERSION ELEMENT, AND PHOTOCHEMICAL BATTERY

(75) Inventors: Yoshihisa Kakuta, Ichihara (JP); Takafumi Iwasa, Ichihara (JP)

(73) Assignee: Ube Industries, Ltd., Yamaguchi (JP)

( * ) Notice: Subject to any disclaimer, the term of this patent is extended or adjusted under 35 U.S.C. 154(b) by 697 days.

(21) Appl. No.: 11/575,745

(22) PCT Filed: Oct. 3, 2005

(86) PCT No.: PCT/JP2005/018289

§ 371 (c)(1),
(2), (4) Date: Mar. 21, 2007

(87) PCT Pub. No.: WO2006/038587

PCT Pub. Date: Apr. 13, 2006

(65) Prior Publication Data

US 2008/0015356 A1    Jan. 17, 2008

(30) Foreign Application Priority Data

Oct. 1, 2004   (JP) .............................. 2004-290075
Oct. 1, 2004   (JP) .............................. 2004-290076

(51) Int. Cl.
*C07F 9/00*        (2006.01)
(52) U.S. Cl. ........................................ 546/10
(58) Field of Classification Search ................... 546/10
See application file for complete search history.

(56) References Cited

FOREIGN PATENT DOCUMENTS

| EP | 1 052 661 A2 | 11/2000 |
|---|---|---|
| JP | 2000-323191 | 11/2000 |
| JP | 2004-359677 | 12/2004 |

OTHER PUBLICATIONS

K. Kalyanasundaram, et al., "Tuning of the CT excited state and validity of the energy gap law in mixed ligand complexes of Ru (II) containing 4,4'-dicarboxy-2,2'-bipyridine," Chemical Physics Letters, vol. 193, No. 4, pp. 292-297, May 29, 1992.

Masa-aki Haga, et al., "Electrochemistry of Symmetrical and Asymmetrical Dinuclear Ruthenium, Osmium, and Mixed-Metal 2,2'-Bipyridine Complexes Bridged by 2,2'-Bibenzimidazolate," Inorganic Chemistry, vol. 30, No. 3, pp. 475-480, 1991.

Anthea C. Lees, et al., "Photophysical Properties of $TiO_2$ Surfaces Modified with Dinuclear RuRu and RuOs Polypyridyl Complexes," Inorganic Chemistry, vol. 40, No. 21, pp. 5343-5349, 2001.

Bobak Gholamkhass, et al., "Adjacent-versus Remote-Site Electron Injection in $TiO_2$ Surfaces Modified with Binuclear Ruthenium Complexes," Inorganic Chemistry, vol. 42, No. 9, pp. 2919-2932, 2003.

Cornelis J. Kleverlaan, et al., "Stepwise Charge Separation in Heterotriads. Binuclear Ru(II)-Rh(III) Complexes on Nanocrystalline Titanium Dioxide," J. Am. Chem. Soc. vol. 122, No. 12, pp. 2840-2849, 2000.

Partha Majumdar, et al.,"Biimidazole complexes of $ML_2^{2+}$[M=Ru or Os, L=2-(phenylazo)-pyridine]. Synthesis, structure and redox properties of mono- and di-nuclear complexes," J. Chem. Soc., Dalton Trans., pp. 1569-1574, 1998.

D. Paul Rillema, et al., "Multimetallic Ruthenium (II) Complexes Based on Biimidazole and Bibenzimidazole: Effect of Dianionic Bridging Ligands on Redox and Spectral Properties," Inorganic Chemistry, vol. 29, No. 2, pp. 167-175, 1990.

M. T. Indelli, et al., Four Intercomponent Processes in a Ru(II)-Rh(III) Polypyridine Dyad: Electron Transfer from Excited Donor, Electron Transfer to Excited Acceptor, Charge Recombination, and Electronic Energy Transfer, J. Am. Chem. Soc., 1994, vol. 116 No. 9, 1994, 3768-3779.

*Primary Examiner*—Taofiq A Solola
(74) *Attorney, Agent, or Firm*—Knobbe Martens Olson & Bear LLP

(57) ABSTRACT

A novel binuclear metal complex according to the present invention is an asymmetric binuclear metal complex represented by the general formula: $(L^1)_2M^1(BL)M^2(L^2)_2(X)_n$, wherein $M^1$ and $M^2$, which may be identical or different, represent a transition metal; $L^1$ and $L^2$, which are different, represent a chelate ligand capable of polydentate coordination and two $L^1$s may be different and two $L^2$s may be different; BL represents a bridge ligand having at least two heteroatom-containing cyclic structures, the heteroatoms contained in the cyclic structures being ligand atoms coordinating to $M^1$ and $M^2$; X represents a counter ion; and n is the number of counter ions needed to neutralize the charge of the complex. And the binuclear metal complex is useful as a metal complex dye.

8 Claims, 15 Drawing Sheets

① Glass
② Transparent conductive layer
③ Platinum layer
④ Electrolytic solution
⑤ Dye-adsorbed porous oxide semiconductor film

BINUCLEAR METAL COMPLEX, METAL COMPLEX DYE, PHOTOELECTRIC CONVERSION ELEMENT, AND PHOTOCHEMICAL BATTERY

This application is the U.S. National Phase under 35 U.S.C. §371 of International Application PCT/JP2005/18289, filed Oct. 3, 2005, which claims priority to Japanese Patent Application No. 2004-290075, filed Oct. 1, 2004, and Japanese Patent Application No. 2004-290076, filed Oct. 1, 2004. The International Application is published under PCT Article 21(2) in a language other than English.

TECHNICAL FIELD

The present invention relates to a novel binuclear metal complex.

The present invention also relates to a metal complex dye having a high absorbance index and improved electron transfer; a photoelectric conversion element comprising an oxide semiconductor photosensitized by the metal complex dye; and a photochemical battery therewith.

BACKGROUND ART

A solar battery is greatly expected to be a clean regenerative energy source, and researches have been conducted for practical application of a monocrystalline-silicon, polycrystalline-silicon or amorphous-silicon solar battery and a solar battery containing a compound such as cadmium telluride and indium-copper selenide. For prevalence of it as a household power source, however, any of these batteries faces many problems to be overcome, including a higher production cost, difficulty in ensuring raw material preparation, difficulty in recycling and difficulty in realizing a larger area. Therefore, there have been proposed solar batteries using an organic material in an attempt to achieve a larger area and a lower cost. However, any of these has a conversion efficiency of about 1%, which falls very short of practical use.

Under such circumstances, Graetzel et al. disclosed a photoelectric conversion element comprising semiconductor particles sensitized by a dye and a solar battery, as well as materials and technique for producing such a solar battery in Nature in 1991 (for example, Nature, Vol. 353, p. 737, 1991 (Non-patent document 1) and Japanese Laid-open Patent Publication No. 1989-220380 (Patent document 1)). The battery is a wet solar battery having a porous titania film sensitized by a ruthenium dye as a working electrode. This solar battery has the advantages that it can be provided as an inexpensive photoelectric conversion element because inexpensive materials can be used without highly purification, and that solar light can be converted into electricity over a wide visible light wavelength range because a dye having broad absorption is used. However, the conversion efficiency must be further improved for practical use, and therefore, it has been desired to develop a dye having a higher absorbance index and absorbing higher wavelength light.

Japanese Laid-open Patent Publication No. 2003-261536 (Patent document 2) by the present applicant has disclosed a mononuclear metal complex containing a dipyridyl ligand, which is a metal complex dye useful as a photoelectric conversion element.

"Current Technology in Dye-sensitized Solar Battery" (CMC Co., LTD., published on May 25, 2001, p. 117) (Non-patent document 2) has disclosed a polynuclear β-diketonate complex dye.

Japanese Laid-open Patent Publication No. 2004-359677 (Patent document 3), which is published on Dec. 24, 2004, has disclosed a polynuclear complex comprising a plurality of metals and a plurality of ligands wherein a bridge ligand (BL) coordinating to the plurality of metals has a coordination structure having a conjugated heterocyclic ring and a coordination structure without a conjugated heterocyclic ring, as a novel polynuclear complex improved in photoelectric conversion function of emitting electrons while receiving energy from active ray such as light.

There has been needed a useful and novel metal complex dye as a photoelectric conversion element.

LIST OF REFERENCES

Patent document 1: Japanese Laid-open Patent Publication No. 1989-220380;
Patent document 2: Japanese Laid-open Patent Publication No. 2003-261536;
Patent document 3: Japanese Laid-open Patent Publication No. 2004-359677;
Non-patent document 1: Nature, Vol. 353, p. 737, 1991;
Non-patent document 2: "Current Technology in Dye-sensitized Solar Battery" (CMC Co., LTD., published on May 25, 2001, p. 117).

DISCLOSURE OF THE INVENTION

Problems to be Solved by the Invention

An objective of the present invention is to provide a novel binuclear metal complex useful as a metal complex dye.

Another objective of the present invention is to provide a dye capable of efficiently photosensitizing semiconductor particles, by polynucleating a metal complex dye to improve absorbance index and by adjusting the direction of electron transition from an electrolytic solution side to a porous semiconductor to achieve a smoother electron transfer. A further objective of the present invention is to provide a photoelectric conversion element having a higher photoelectric conversion efficiency by using such a dye and to provide a photochemical battery comprising the photoelectric conversion element.

Means for Solving the Problems

The present invention relates to an asymmetric binuclear metal complex represented by the general formula: $(L^1)_2M^1(BL)M^2(L^2)_2(X)_n$, wherein $M^1$ and $M^2$, which may be identical or different, represent a transition metal;

$L^1$ and $L^2$, which are different, represent a chelate ligand capable of polydentate coordination and two $L^1$s may be different and two $L^2$s may be different;

BL represents a bridge ligand having at least two heteroatom-containing cyclic structures, the heteroatoms contained in the cyclic structures being ligand atoms coordinating to $M^1$ and $M^2$;

X represents a counter ion; and n is the number of counter ions needed to neutralize the charge of the complex.

The present invention also relates to the above binuclear metal complex, wherein $L^1$ and $L^2$ represent a chelate ligand capable of bidentate, tridentate or tetradentate coordination.

The present invention also relates to the above binuclear metal complex, wherein $L^1$ and $L^2$ represent a bidentate ligand, which is a bipyridyl, pyridylquinoline, biquinoline or phenanthroline derivative.

The present invention also relates to the above binuclear metal complex, wherein $L^1$ is a ligand substituted with at least one of carboxyl (—COOH) or —COO—.

The present invention also relates to the above binuclear metal complex, wherein BL represents a tetradentate ligand.

The present invention also relates to the above binuclear metal complex, wherein $M^1$ and $M^2$ are independently selected from the group consisting of Group VIII to Group XI transition metals.

The present invention also relates to the above binuclear metal complex, wherein $M^1$ and $M^2$ are independently selected from the group consisting of ruthenium (Ru), osmium (Os), cobalt (Co), nickel (Ni), copper (Cu) and iron (Fe).

And furthermore, the present invention relates to a metal complex dye comprising an asymmetric binuclear metal complex represented by the general formula: $(L^1)_2M^1(BL)M^2(L^2)_2(X)_n$, wherein $M^1$ and $M^2$, which may be identical or different, represent a transition metal;

$L^1$ and $L^2$, which are different, represent a chelate ligand capable of polydentate coordination and two $L^1$s may be different and two $L^2$s may be different;

X represents a counter ion;

n is the number of counter ions needed to neutralize the charge of the complex;

BL represents a bridge ligand having at least two heteroatom-containing cyclic structures, the heteroatoms contained in the cyclic structures being ligand atoms coordinating to $M^1$ and $M^2$; and $L^1$ contains a substituent capable of attaching to a semiconductor particle; and LUMOs are predominantly distributed in $(L^1)_2M^1$.

The present invention also relates to a photoelectric conversion element comprising semiconductor particles sensitized by the above metal complex dye.

The present invention also relates to the above photoelectric conversion element, wherein the semiconductor particle is selected from the group consisting of titanium oxide, zinc oxide and tin oxide.

The present invention also relates to a photochemical battery comprising the above photoelectric conversion element.

Effect of the Invention

As compared to an existing dye exhibiting a high photoelectric conversion efficiency which is used as a comparative dye, a metal complex dye according to the present invention has a higher absorbance index and an improved short-circuit current density per 1 mol (1 molecule) of a complex. Furthermore, a higher photoelectric conversion efficiency can be achieved by using a dye having an appropriate molecular orbital distribution. A photochemical battery comprising such a photoelectric conversion element is very effective as a solar battery. Additionally, in contrast to an existing dye exhibiting a high photoelectric conversion efficiency, a metal complex dye according to the present invention does not have a —NCS group, which may decompose readily, in the molecule and therefore exhibits high heat resistance.

(Description of the Symbols)

1: glass, 2: transparent conductive layer, 3: platinum layer, 4: electrolytic solution, 5: dye-adsorbed porous oxide semiconductor film.

Figure 21:
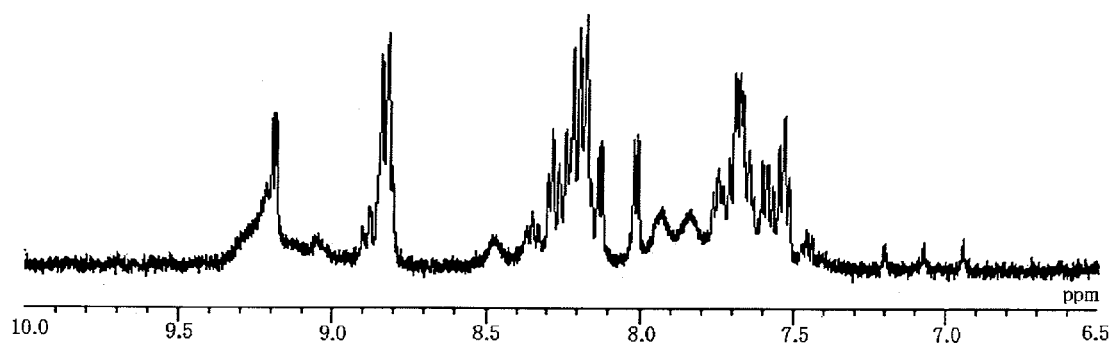

FIG. 21 shows a $^1$H-NMR spectrum of the binuclear metal complex (D-16) prepared in Example 18 in dimethyl sulfoxide-d6.

Figure 22:
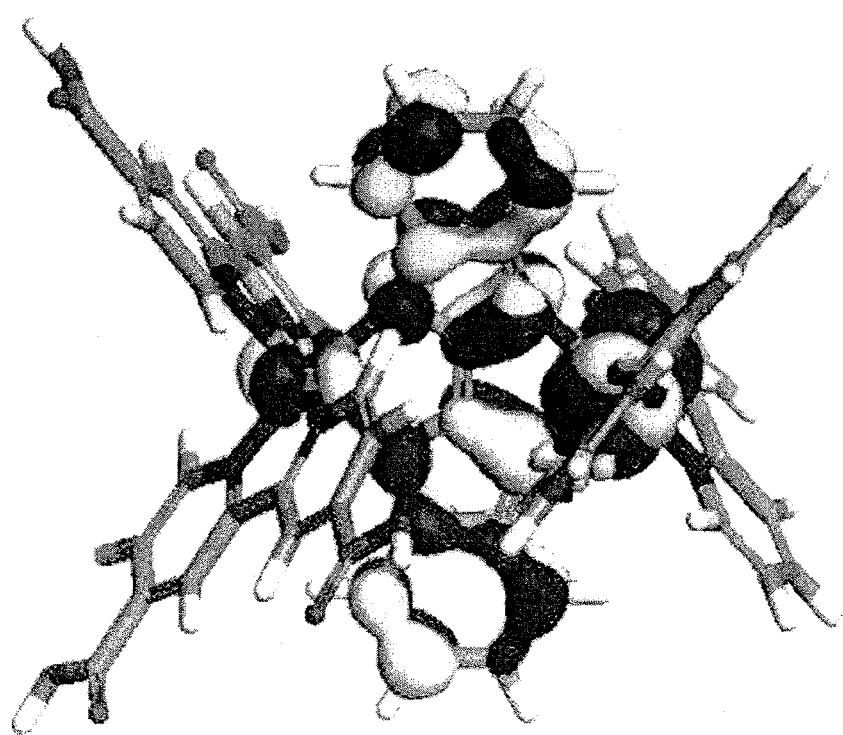

FIG. 22 shows a visualized shape of a HOMO (including a next HOMO) orbital in the structure shown in the binuclear metal complex dye (D-4) prepared in Example 4.

Figure 23:
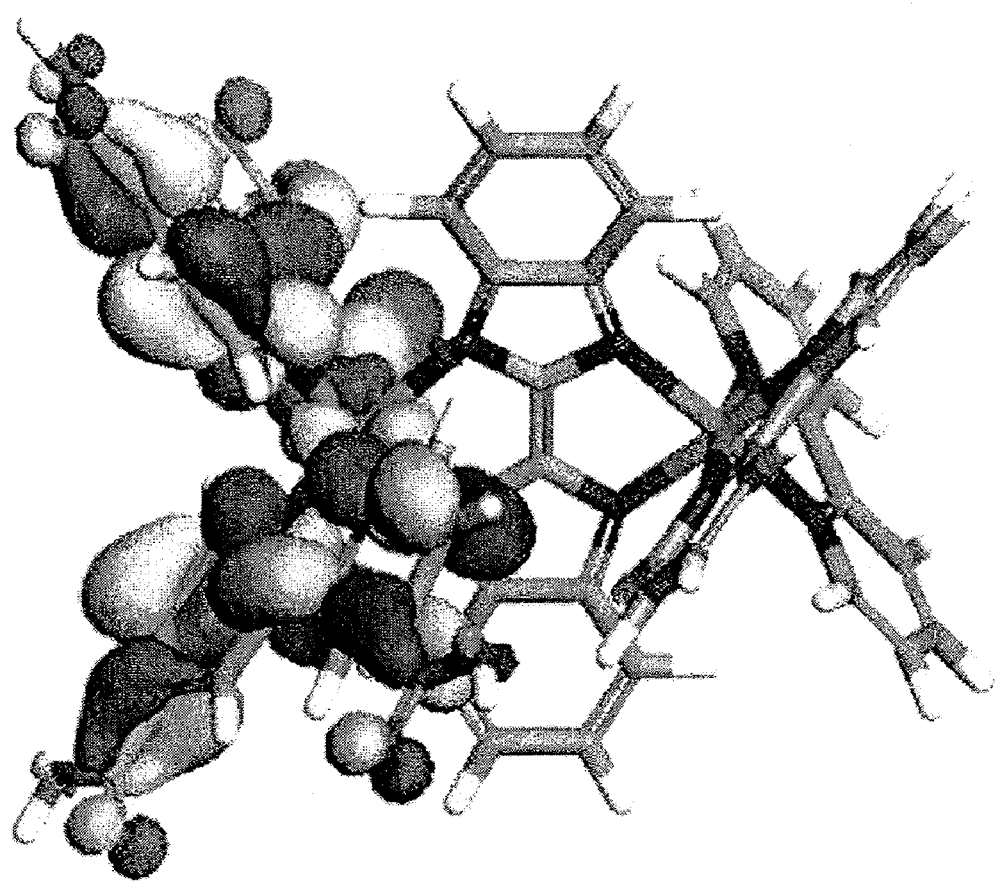

FIG. 23 shows a visualized shape of a LUMO (including a next LUMO) orbital in the structure shown in the binuclear metal complex dye (D-4) prepared in Example 4.

Figure 24:
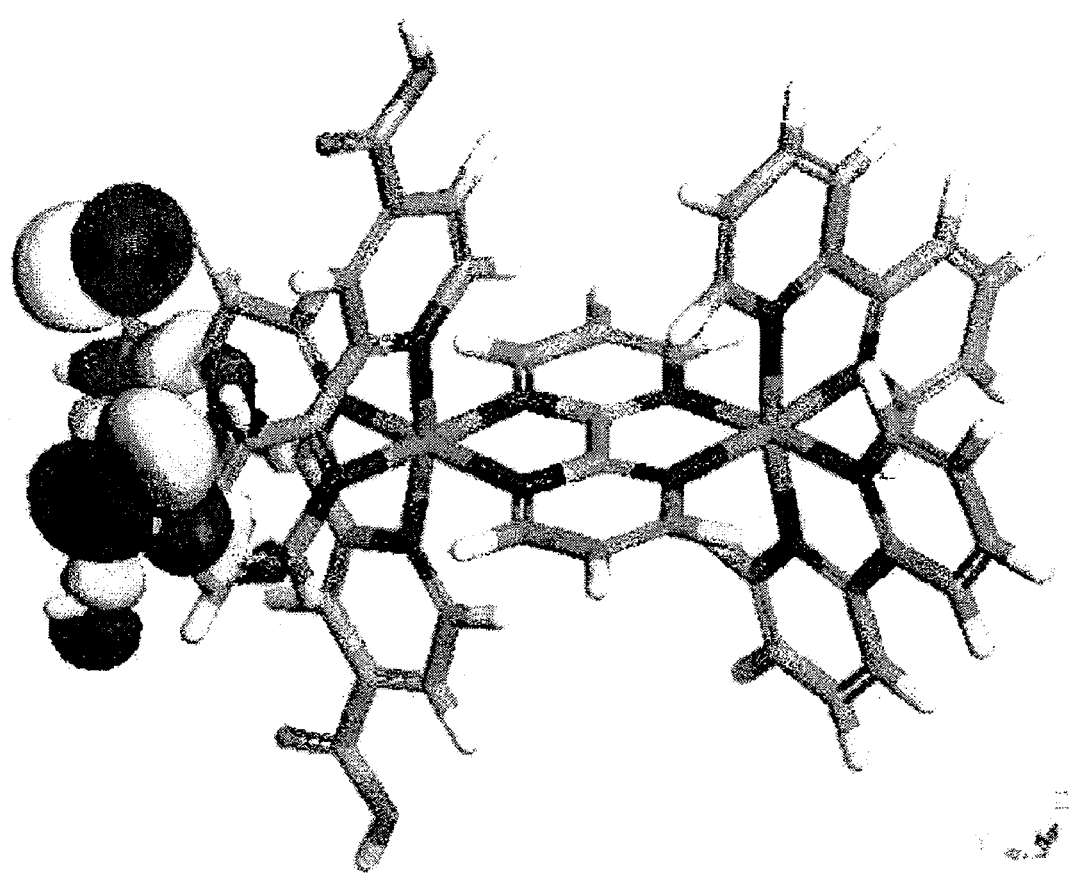

FIG. 24 shows a visualized shape of a HOMO (including a next HOMO) orbital in the structure shown in the binuclear metal complex dye (D-16) prepared in Example 18.

Figure 25:
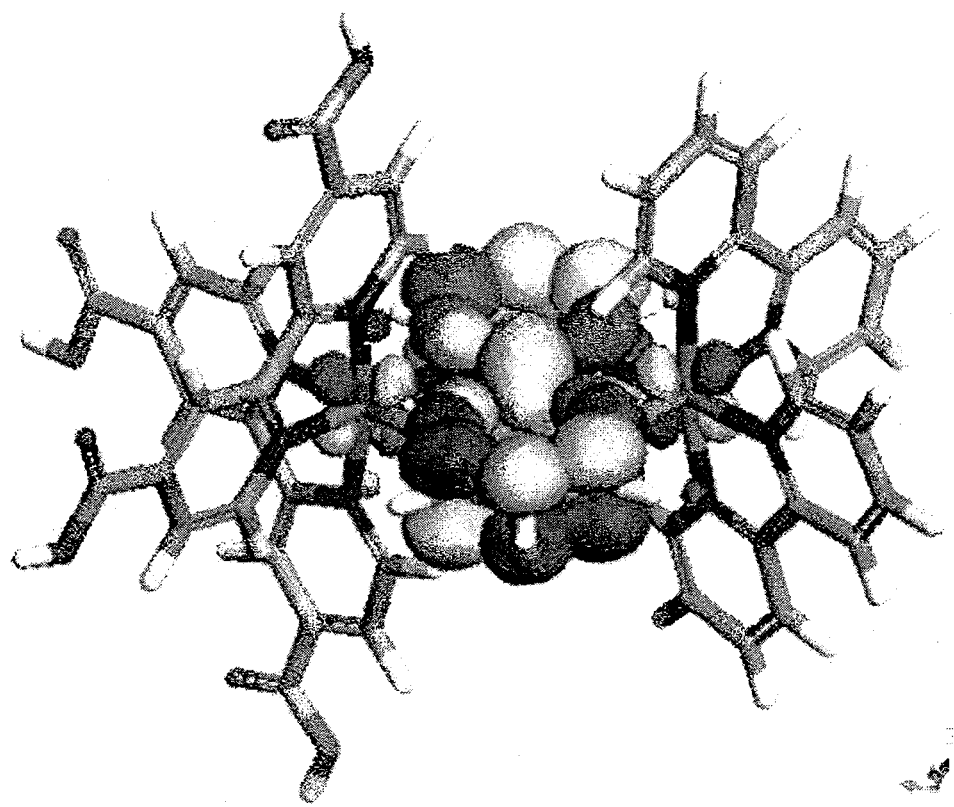

FIG. 25 shows a visualized shape of a LUMO (including a next LUMO) orbital in the structure shown in the binuclear metal complex dye (D-16) prepared in Example 18.

Figure 26:
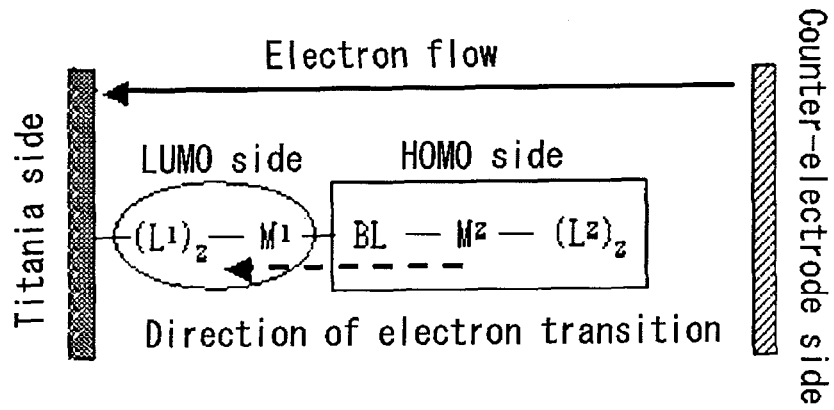

FIG. 26 conceptually shows an electron-transition direction in HOMO-LUMO in a preferable binuclear metal complex dye according to the present invention and electron flow within a photochemical battery circuit.

Figure 27:
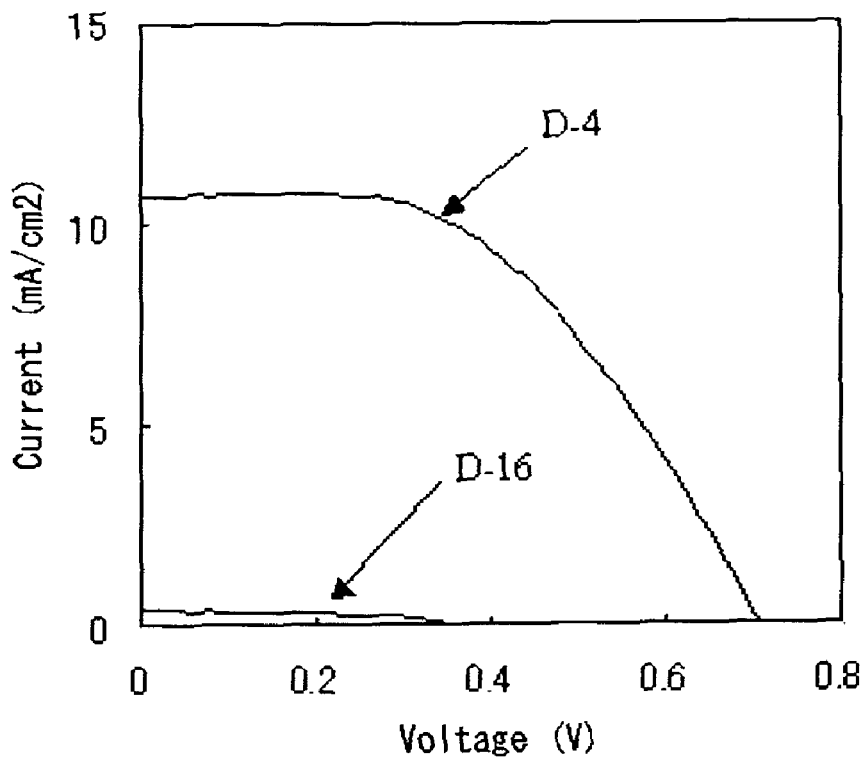

FIG. 27 shows a current-voltage characteristic curve of the photochemical battery produced using the binuclear metal complex dyes (D-4) and (D-16) prepared in Examples 4 and 18, respectively.

Figure 28:
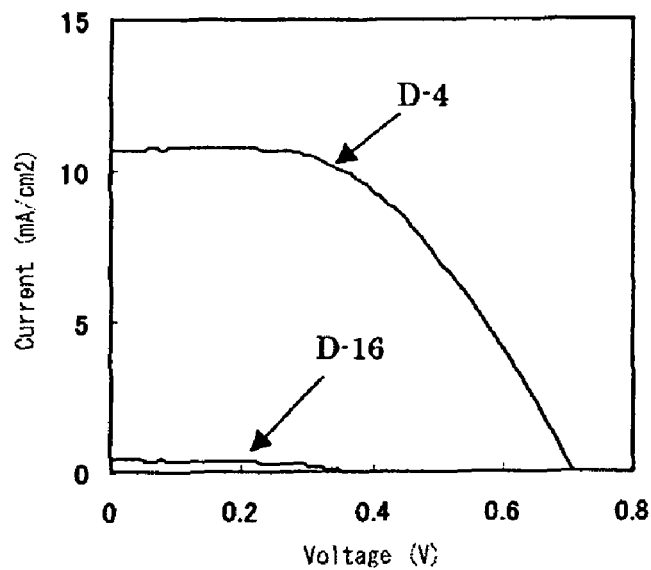

FIG. 28 shows a current-voltage characteristic curve of the photochemical battery produced using the binuclear metal complex dyes (D-4) and (D-16) prepared in Examples 4 and 18, respectively.

BEST MODE FOR CARRYING OUT THE INVENTION

In the asymmetric binuclear metal complex represented by the general formula: $(L^1)_2M^1(BL)M^2(L^2)_2(X)_n$ according to the present invention, $M^1$ and $M^2$ represent a transition metal, preferably a transition metal in Groups VIII to XI. Specifically, ruthenium (Ru), osmium (Os), cobalt (Co), nickel (Ni), copper (Cu) or iron (Fe) is preferable. Among them, ruthenium (Ru) and osmium (Os) are preferable, and ruthenium (Ru) is particularly preferable.

$M^1$ and $M^2$ may be identical or different.

$L^1$ and $L^2$ represent a chelate ligand capable of polydentate coordination, preferably a chelate ligand capable of bidentate, tridentate or tetradentate coordination, more preferably a chelate ligand capable of bidentate coordination. Specific examples include derivatives of 2,2'-bipyridine, 1,10-phenanthroline, 2-(2-pyridinyl)quinoline, 2,2'-biquinoline and the like. $L^1$ and $L^2$ are different. Two $L^1$s may be different and two $L^2$s may be also different.

When the binuclear metal complex according to the present invention is a metal complex dye used in a photoelectric conversion element, $L^1$ contains at least one substituent capable of attaching to a semiconductor particle.

Examples of a substituent in $L^1$ capable of attaching to a semiconductor particle include carboxyl (—COOH), amino (—NH$_2$), hydroxy (—OH), sulfate (—SO$_3$H), phosphate (—PO$_3$H$_2$) and nitro (—NO$_2$). Among them, carboxyl (—COOH) is preferable. The hydrogen in a carboxyl group may be replaced with a cation including a quaternary ammonium such as tetrabutylammonium and an alkali metal ion such as sodium ion. Alternatively, the hydrogen may be liberated.

Furthermore, $L^1$ may or may not contain a substituent other than the substituent capable of attaching to a semiconductor particle. Examples of such a substituent include alkyl such as methyl and ethyl, and alkoxy such as methoxy and ethoxy.

When the binuclear metal complex according to the present invention is a metal complex dye used in a photoelectric conversion element, $L^1$ is preferably a ligand in which LUMOs are predominantly distributed in the $(L^1)_2M^1$ moiety. The phrase, "LUMOs are predominantly distributed in the $(L^1)_2M^1$ moiety" as used herein means that there are more LUMOs in the $(L^1)_2M^1$ moiety than in the $(L^2)_2M^2$ moiety. The structure of the binuclear metal complex where the $(L^1)_2M^1$ predominantly have LUMOs to which an electron is excited by irradiation with light such as solar light allows smooth electron transfer from an electrolyte to a photoelectric conversion element (anode), thereby obtaining an efficient photochemical battery, when a photochemical battery is produced using a photoelectric conversion element comprising semiconductor particles sensitized by the binuclear metal complex.

An LUMO was calculated using software, Cerius$^2$ or Material Studio. The method was optimized for a metal complex structure by DFT (density functional theory) using the DMol$^3$ module. Suitable exchange correlation functions therefor include, but not limited to, VWN and BLYP methods. A suitable basis function is, but not limited to, DNP.

An energy state was calculated using the obtained structure, and a exchange correlation function therefor is, but not limited to, BLYP and PBE, and a suitable basis function is, but not limited to, DNP.

$L^1$ may be the ligand represented by the following formula ($L^1$-A).

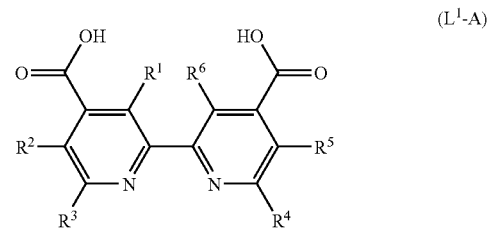

(L$^1$-A)

In the above formula, H in —COOH may be liberated. $R^1$, $R^2$, $R^3$, $R^4$, $R^5$ and $R^6$ independently represent hydrogen, alkoxy, or substituted or unsubstituted hydrocarbon, or alternatively, two or more of these together with the carbon atoms to which they are bound may form a substituted or unsubstituted aromatic hydrocarbon ring, or a substituted or unsubstituted aliphatic hydrocarbon ring.

$R^1$ to $R^6$ are preferably hydrogen, alkyl or alkoxy, more preferably hydrogen or alkyl. The alkyl is preferably one containing up to six carbon atoms, more preferably methyl or ethyl. The alkoxy is preferably one containing up to six carbon atoms, more preferably methoxy or ethoxy.

It is also preferable that $R^2$ and $R^3$, $R^4$ and $R^5$, or $R^1$ and $R^6$ together with the carbon atoms to which they are bound form a six-membered aromatic hydrocarbon ring which may be substituted with a substituent. Examples of the substituent in the aromatic hydrocarbon ring include alkyl such as methyl and ethyl, and alkoxy such as methoxy and ethoxy.

$R^1$ to $R^6$ are particularly preferably hydrogen.

Specific examples of $L^1$ include, but are not limited to, the ligands represented by the following formulas ($L^1$-1) to ($L^1$-4).

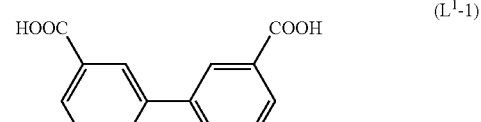

(L$^1$-1)

2,2'-Bipyridine-4,4'-dicarboxylic acid (H$_2$dcbpy)

-continued

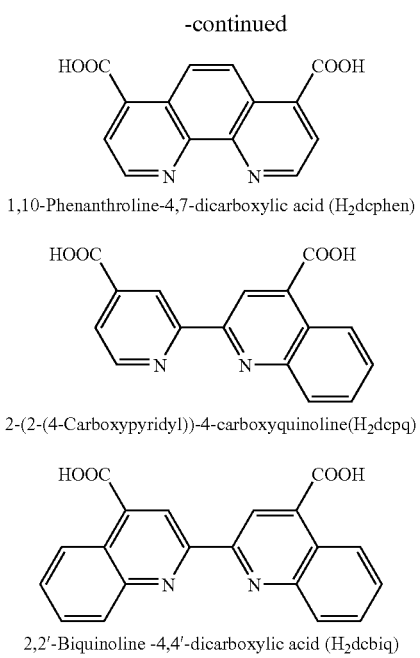

1,10-Phenanthroline-4,7-dicarboxylic acid (H₂dcphen)  (L¹-2)

2-(2-(4-Carboxypyridyl))-4-carboxyquinoline(H₂dcpq)  (L¹-3)

2,2'-Biquinoline-4,4'-dicarboxylic acid (H₂dcbiq)  (L¹-4)

In these formulas (L¹-1) to (L¹-4), the heterocyclic ring and the benzene ring may be substituted with a substituent, and H in —COOH may be liberated. Examples of the substituent include alkyl containing up to six carbon atoms such as methyl and ethyl, and alkoxy containing up to six carbon atoms such as methoxy and ethoxy.

As described above, $L^2$ is a chelate ligand capable of polydentate coordination, preferably a chelate ligand capable of bidentate, tridentate or tetradentate coordination, more preferably a chelate ligand capable of bidentate coordination. Specific examples include derivatives of 2,2'-bipyridine, 1,10-phenanthroline, 2-(2-pyridinyl)quinoline, 2,2'-biquinoline and the like.

$L^2$ may or may not contain a substituent. Examples of the substituent in $L^2$ include alkyl such as methyl and ethyl, aryl such as phenyl and tolyl, alkoxy such as methoxy and ethoxy, and hydroxy (—OH). An electron-donating group is particularly preferable.

$L^2$ may be the ligand represented by the following formula (L²-A).

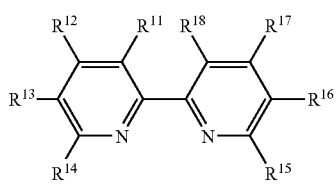
(L²-A)

In the above formula, $R^{11}$, $R^{12}$, $R^{13}$, $R^{14}$, $R^{15}$, $R^{16}$, $R^{17}$ and $R^{18}$ independently represent hydrogen, alkoxy, hydroxy, or substituted or unsubstituted hydrocarbon, or alternatively, two or more of these together with the carbon atoms to which they are bound may form a substituted or unsubstituted aromatic hydrocarbon ring, or a substituted or unsubstituted aliphatic hydrocarbon ring.

$R^{11}$ to $R^{18}$ are preferably hydrogen, alkyl or alkoxy, more preferably hydrogen or alkyl. The alkyl is preferably one containing up to six carbon atoms, more preferably methyl or ethyl. The alkoxy is preferably one containing up to six carbon atoms, more preferably methoxy or ethoxy.

It is also preferable that adjacent two of $R^{11}$ to $R^{18}$ or $R^{11}$ and $R^{18}$ together with the carbon atoms to which they are bound form a six-membered aromatic hydrocarbon ring which may be substituted with a substituent. Examples of the substituent in the aromatic hydrocarbon ring include alkyl such as methyl and ethyl, and alkoxy such as methoxy and ethoxy.

Particularly preferably, $R^{11}$ to $R^{18}$ are hydrogen or methyl. Alternatively, it is also particularly preferable that $R^{11}$ and $R^{18}$ together with the carbon atoms to which they are bound form a six-membered aromatic hydrocarbon ring which may be substituted with a substituent such as methyl, and $R^{12}$ to $R^{17}$ are hydrogen or methyl, more preferably hydrogen.

Specific examples of $L^2$ include, but are not limited to, the ligands represented by the following formulas (L²-1) to (L²-4).

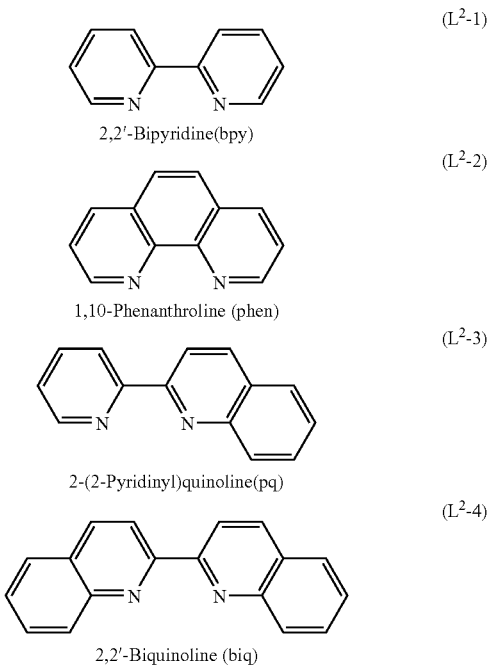

2,2'-Bipyridine(bpy)  (L²-1)

1,10-Phenanthroline (phen)  (L²-2)

2-(2-Pyridinyl)quinoline(pq)  (L²-3)

2,2'-Biquinoline (biq)  (L²-4)

In these formulas (L²-1) to (L²-4), the heterocyclic ring and the benzene ring may be substituted with a substituent. Examples of the substituent include alkyl containing up to six carbon atoms, alkoxy containing up to six carbon atoms, phenyl optionally substituted with a substituent such as methyl, and hydroxy.

BL is a bridge ligand and has a heteroatom-containing cyclic structure. The heteroatom contained in the cyclic structure (conjugated heterocyclic ring) is the ligand atom coordinating to $M^1$ and $M^2$. The heteroatom may be, for example, nitrogen, oxygen, sulfur or phosphorus.

BL is preferably a tetradentate ligand. And it is more preferably anionic. BL may or may not have a substituent on the cyclic structure (conjugated heterocyclic ring).

BL may be the ligand represented by the following formula (BL-A).

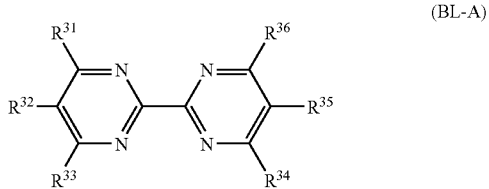

(BL-A)

In the above formula, $R^{31}$, $R^{32}$ and $R^{33}$ independently represent hydrogen, or substituted or unsubstituted hydrocarbon, or alternatively, two or more of these together with the carbon atoms to which they are bound may form a substituted or unsubstituted aromatic hydrocarbon ring, or a substituted or unsubstituted aliphatic hydrocarbon ring. $R^{34}$, $R^{35}$ and $R^{36}$ independently represent hydrogen, or substituted or unsubstituted hydrocarbon, or alternatively, two or more of these together with the carbon atoms to which they are bound may form a substituted or unsubstituted aromatic hydrocarbon ring, or a substituted or unsubstituted aliphatic hydrocarbon ring.

$R^{31}$ to $R^{36}$ are preferably hydrogen, alkyl or alkoxy, more preferably hydrogen or alkyl. The alkyl is preferably one containing up to six carbon atoms, more preferably methyl or ethyl. The alkoxy is preferably one containing up to six carbon atoms, more preferably methoxy or ethoxy.

It is also preferable that adjacent two of $R^{31}$ to $R^{36}$ together with the carbon atoms to which they are bound form a six-membered aromatic hydrocarbon ring which may be substituted with a substituent. Examples of the substituent in the aromatic hydrocarbon ring include alkyl such as methyl and ethyl, and alkoxy such as methoxy and ethoxy.

$R^{31}$ to $R^{36}$ are particularly preferably hydrogen or methyl, and $R^{31}$ to $R^{36}$ are further preferably hydrogen.

BL may be the ligand represented by the following formula (BL-B).

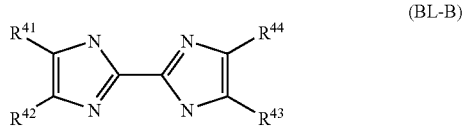

(BL-B)

In the above formula, $R^{41}$ and $R^{42}$ independently represent hydrogen, or substituted or unsubstituted hydrocarbon, or alternatively, these together with the carbon atoms to which they are bound may form a substituted or unsubstituted aromatic hydrocarbon ring, or a substituted or unsubstituted aliphatic hydrocarbon ring. $R^{43}$ and $R^{44}$ independently represent hydrogen, or substituted or unsubstituted hydrocarbon, or alternatively, these together with the carbon atoms to which they are bound may form a substituted or unsubstituted aromatic hydrocarbon ring, or a substituted or unsubstituted aliphatic hydrocarbon ring.

$R^{41}$ to $R^{44}$ are preferably hydrogen, alkyl or alkoxy, more preferably hydrogen or alkyl. The alkyl is preferably one containing up to six carbon atoms, more preferably methyl or ethyl. The alkoxy is preferably one containing up to six carbon atoms, more preferably methoxy or ethoxy.

It is also preferable that $R^{41}$ and $R^{42}$ or $R^{43}$ and $R^{44}$ together with the carbon atoms to which they are bound form a six-membered aromatic hydrocarbon ring which may be substituted with a substituent. Examples of the substituent in the aromatic hydrocarbon ring include alkyl such as methyl and ethyl, and alkoxy such as methoxy and ethoxy.

$R^{41}$ to $R^{44}$ are particularly preferably hydrogen or methyl, and $R^{41}$ to $R^{44}$ are further preferably hydrogen. It is also particularly preferable that $R^{41}$ and $R^{42}$ or $R^{43}$ and $R^{44}$ together with the carbon atoms to which they are bound form a six-membered aromatic hydrocarbon ring which may be substituted with a substituent such as methyl.

Among the ligands represented by the above formula (BL-B), the ligand represented by the following formula (BL-C) is preferable.

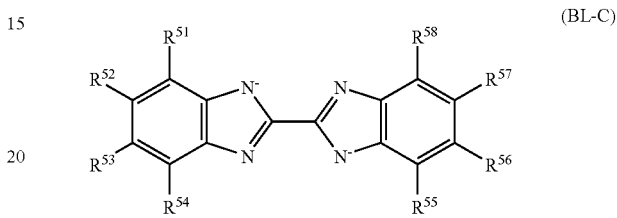

(BL-C)

In the above formula, $R^{51}$, $R^{52}$, $R^{53}$ and $R^{54}$ independently represent hydrogen, or substituted or unsubstituted hydrocarbon, or alternatively, two or more of these together with the carbon atoms to which they are bound may form a substituted or unsubstituted aromatic hydrocarbon ring, or a substituted or unsubstituted aliphatic hydrocarbon ring. $R^{55}$, $R^{56}$, $R^{57}$ and $R^{58}$ independently represent hydrogen, or substituted or unsubstituted hydrocarbon, or alternatively, two or more of these together with the carbon atoms to which they are bound may form a substituted or unsubstituted aromatic hydrocarbon ring, or a substituted or unsubstituted aliphatic hydrocarbon ring.

$R^{51}$ to $R^{58}$ are preferably hydrogen, alkyl or alkoxy, more preferably hydrogen or alkyl. The alkyl is preferably one containing up to six carbon atoms, more preferably methyl or ethyl. The alkoxy is preferably one containing up to six carbon atoms, more preferably methoxy or ethoxy.

It is also preferable that adjacent two of $R^{51}$ to $R^{58}$ together with the carbon atoms to which they are bound form a six-membered aromatic hydrocarbon ring which may be substituted with a substituent. Examples of the substituent in the aromatic hydrocarbon ring include alkyl such as methyl and ethyl, and alkoxy such as methoxy and ethoxy.

$R^{51}$ to $R^{58}$ are particularly preferably hydrogen or methyl, and $R^{51}$ to $R^{58}$ are further preferably hydrogen.

Specific examples of BL include, but are not limited to, the ligands represented by the following formulas (BL-1) to (BL-4).

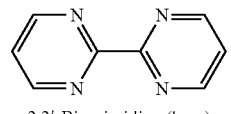

2,2'-Bipyrimidine (bpm)

(BL-1)

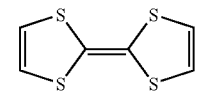

Tetrathiafluvalene (TTF)

(BL-2)

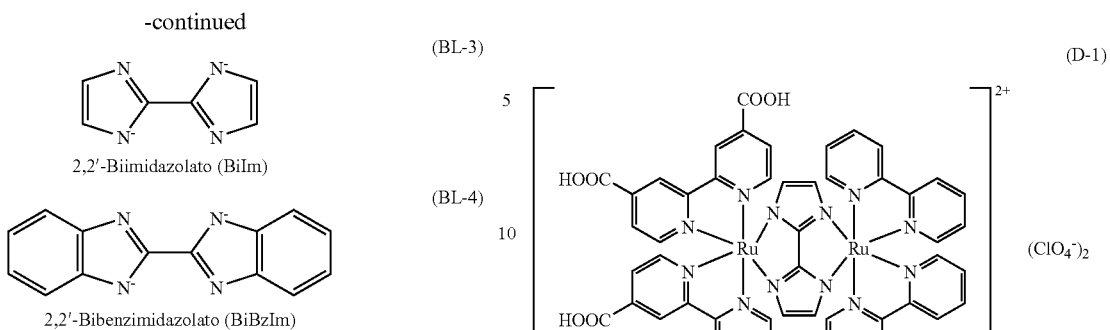

In these formulas (BL-1) to (BL-4), the heterocyclic ring and the benzene ring may be substituted with a substituent. Examples of the substituent include alkyl containing up to six carbon atoms, alkoxy containing up to six carbon atoms. Alternatively, adjacent two of the carbon atoms on the benzene ring in the formula (BL-4) may form a new benzene ring which may be substituted with a substituent.

In the case of a metal complex dye used in a photoelectric conversion element, BL is preferably the ligand represented by the above formula (BL-3) or (BL-4).

$(L^1)_2M^1(BL)M^2(L^2)_2(X)_n$ may contain water or an organic solvent as a crystal solvent. Examples of the organic solvent include DMSO, acetonitrile, DMF, DMAC and methanol. There are no particular restrictions to the number of crystal solvents.

X is a counter ion, which is an anion when the complex $[(L^1)_2M^1(BL)M^2(L^2)_2]$ is a cation, while being a cation when the complex $[(L^1)_2M^1(BL)M^2(L^2)_2]$ is an anion. N is the number of counter ions needed to neutralize the charge of the complex.

When the counter ion is an anion, specific examples of X include hexafluorophosphate, perchlorate, tetraphenylborate, tetrafluoroborate, trifluoromethanesulfonate, thiocyanate, sulfate and nitrate ions, as well as halide ions such as chloride and iodide ions.

When the counter ion is a cation, specific examples of X include ammonium ion, tetrabutylammonium ion, alkali metal ions such as sodium ion, and proton.

A particularly preferable metal complex dye is the above metal complex in which $L^1$ is a ligand represented by the above formula ($L^1$-1) (including that in which H in —COOH is liberated and that in which the heterocyclic ring and the benzene ring have further a substituent); $L^2$ is a ligand represented by the above formula ($L^2$-1) or ($L^2$-2) (including that in which the heterocyclic ring and the benzene ring have a substituent); BL is a ligand represented by the above formula (BL-3) or (BL-4) (including that in which the heterocyclic ring and the benzene ring have a substituent); and $M^1$ and $M^2$ are independently selected from the group consisting of ruthenium (Ru), osmium (Os), cobalt (Co), nickel (Ni), copper (Cu) and iron (Fe).

Specific examples of an asymmetric binuclear metal complex represented by the general formula: $(L^1)_2M^1(BL)M^2(L^2)_2(X)_n$ according to the present invention include, but are not limited to, those represented by the following formulas (D-1) to (D-16).

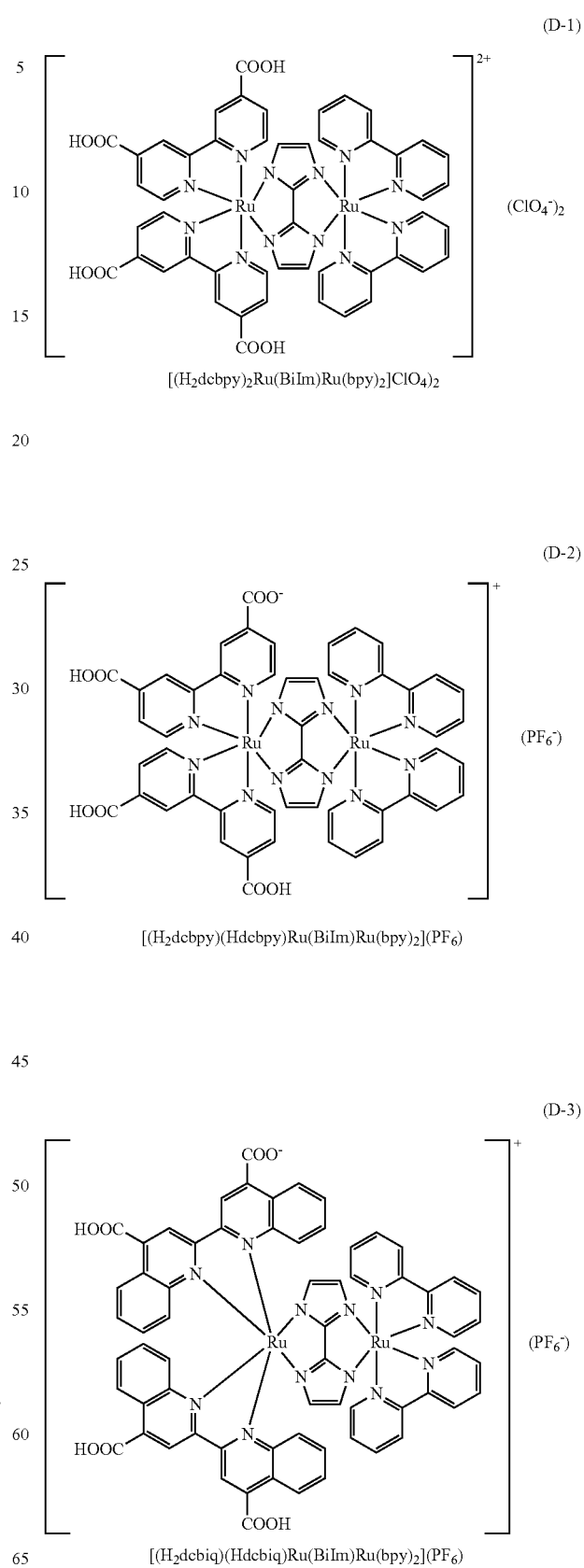

-continued
(D-4)
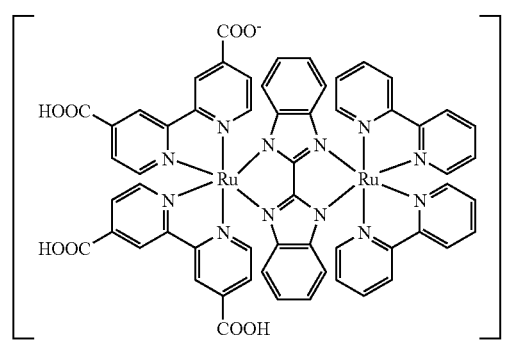
[(H₂dcbpy)(Hdcbpy)Ru(BiBzIm)Ru(bpy)₂](PF₆)
(D-5)
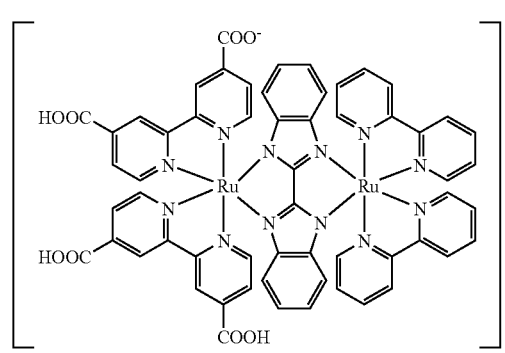
[(H₂dcbpy)(Hdcbpy)Ru(BiBzIm)Ru(bpy)₂](BF₄)
(D-6)
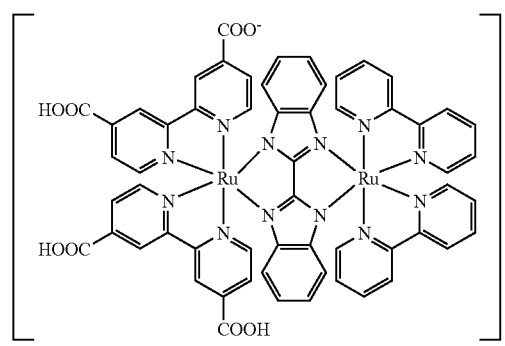
[(H₂dcbpy)(Hdcbpy)Ru(BiBzIm)Ru(bpy)₂](BPh₄)
(D-7)
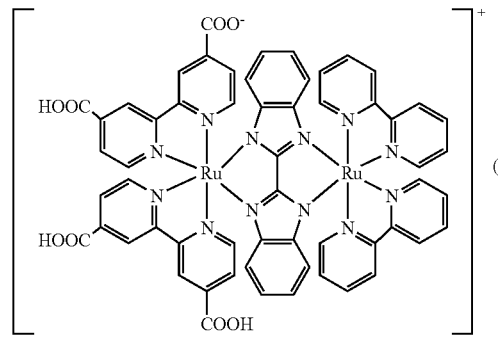
[(H₂dcbpy)(Hdcbpy)Ru(BiBzIm)Ru(bpy)₂](OSO₂CF₃)
-continued
(D-8)
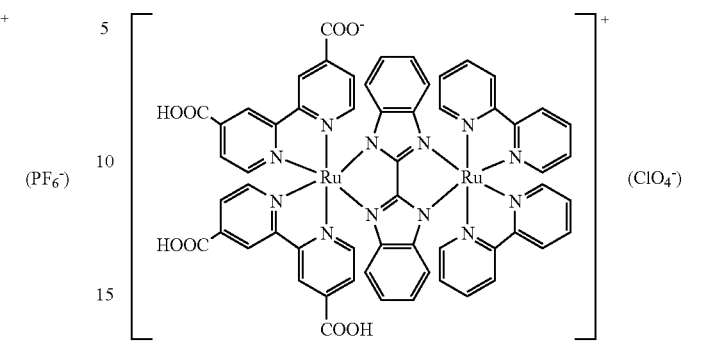
[(H₂dcbpy)(Hdcbpy)Ru(BiBzIm)Ru(bpy)₂](ClO₄)
(D-9)
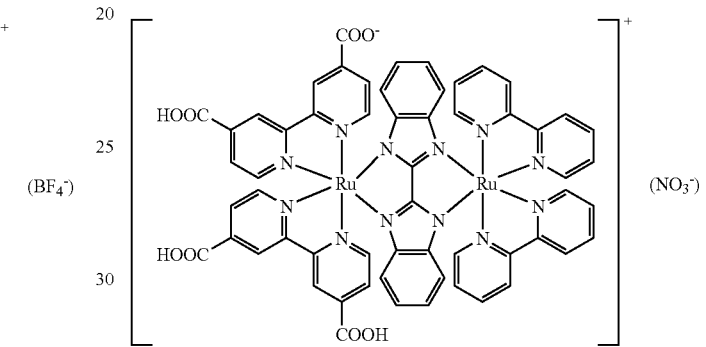
[(H₂dcbpy)(Hdcbpy)Ru(BiBzIm)Ru(bpy)₂](NO₃)
(D-10)
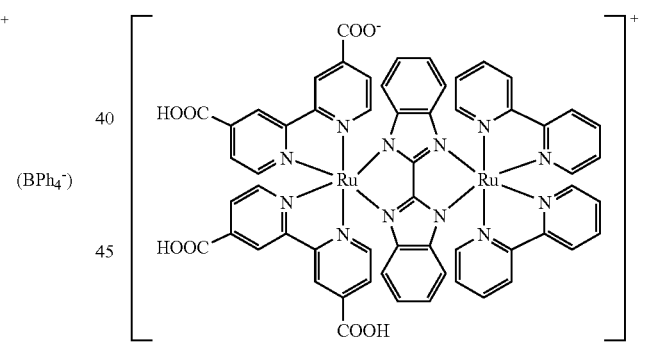
[(H₂dcbpy)(Hdcbpy)Ru(BiBzIm)Ru(bpy)₂](I)
(D-11)
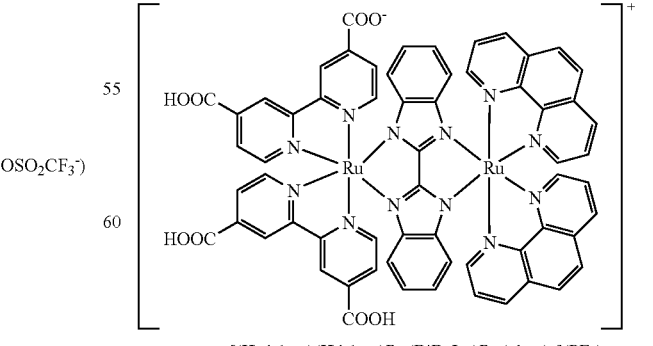
[(H₂dcbpy)(Hdcbpy)Ru(BiBzIm)Ru(phen)₂](PF₆)

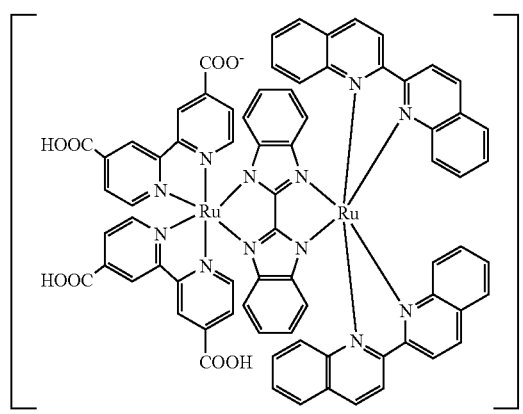

[(H₂dcbpy)(Hdcbpy)Ru(BiBzIm)Ru(biq)₂](PF₆)  (D-12)

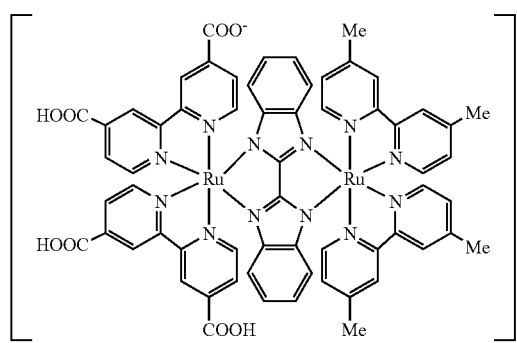

[(H₂dcbpy)(Hdcbpy)Ru(BiBzIm)Ru(dmbpy)₂](PF₆)  (D-13)

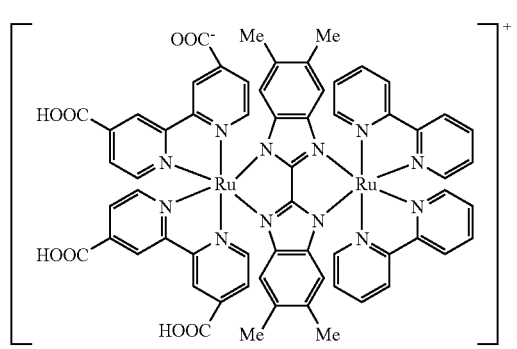

[(H₂dcbpy)(Hdcbpy)Ru(TMBiBzIm)Ru(bpy)₂](PF₆)  (D-14)

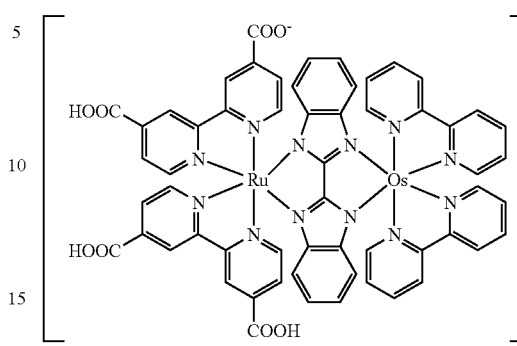

[(H₂dcbpy)(Hdcbpy)Ru(BiBzIm)Os(bpy)₂](PF₆)  (D-15)

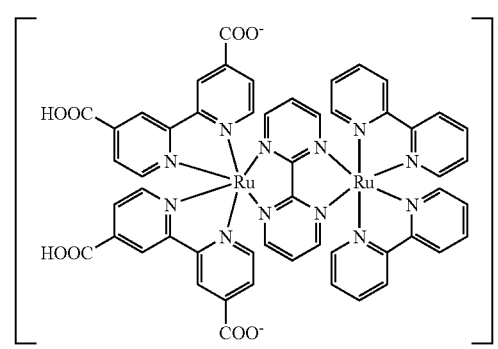

[(Hdcbpy)₂Ru(bpm)Ru(bpy)₂](PF₆)₂  (D-16)

A metal complex according to the present invention can be prepared by reference to the process cited in literatures such as Inorganic Chemistry, Vol. 17 (9), pp. 2660-2666, 1978 and Journal of the American Chemical Society, Vol. 115, pp. 6382-6390, 1993.

A metal complex $(L^1)_2M^1(BL)M^2(L^2)_2(X)_n$ according to the present invention may be prepared, for example, by reacting two mononuclear metal complexes $(L^1)_2M^1Cl_2$ and $(BL)M^2(L^2)_2$ which are synthesized as described below.

A mononuclear metal complex $(L^1)_2M^1Cl_2$ in which $L^1$ is a ligand represented by the above formula ($L^1$-1) and $M^1$ is Ru ($M^1$C-1) can be prepared as shown in the following synthetic scheme.

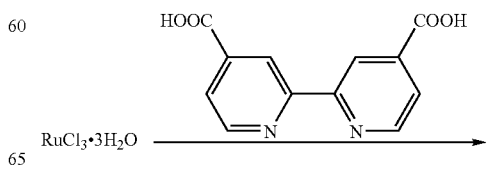

-continued

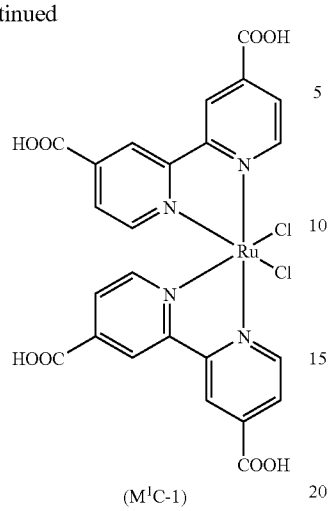

(M¹C-1)

In the above synthetic scheme, a complex in which $L^1$ has a substituent other than carboxyl and a complex in which $M^1$ is a transition metal other than Ru can be synthesized in a similar way.

A mononuclear metal complex $(L^1)_2M^1Cl_2$ in which $L^1$ is a ligand represented by the above formula ($L^1$-4) and $M^1$ is Ru ($M^1$C-2) can be prepared as shown in the following synthetic scheme.

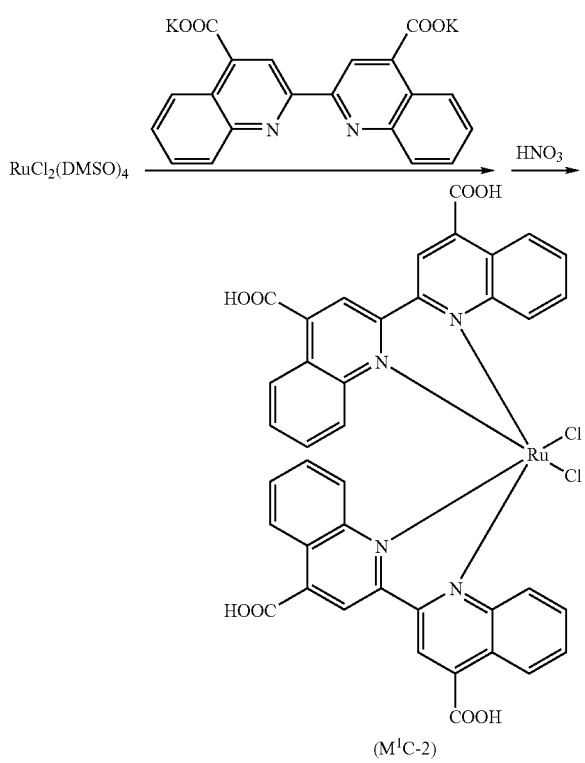

(M¹C-2)

In the above synthetic scheme, a complex in which $L^1$ has a substituent other than carboxyl and a complex in which $M^1$ is a transition metal other than Ru can be synthesized in a similar way.

On the other hand, a mononuclear metal complex $(BL)M^2(L^2)_2$ can be prepared as shown in the following synthetic scheme.

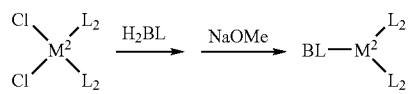

In the above synthetic scheme, $H_2BL$ represents the state where two heteroatoms (nitrogen, and so on) in BL are protonated.

Any of complexes in which BL is a ligand represented by any of the above formulas (BL-1) to (BL-4) (including those having a substituent) and any of complexes in which $L^2$ is a ligand represented by any of the above formulas ($L^2$-1) to ($L^2$-4) (including those having a substituent) can be synthesized as shown in this synthetic scheme. For a complex in which BL is a ligand represented by the above formula (BL-1) (including that having a substituent), the latter reaction step using NaOMe can be omitted, and $M^2(L^2)_2Cl_2$ and BL may be reacted to give $(BL)M^2(L^2)_2$.

$(L^1)_2M^1Cl_2$ ($M^1C$) and $(BL)M^2(L^2)_2$ ($M^2C$) thus synthesized can be reacted as shown in the following synthetic scheme to give $(L^1)_2M^1(BL)M^2(L^2)_2(X)_n$.

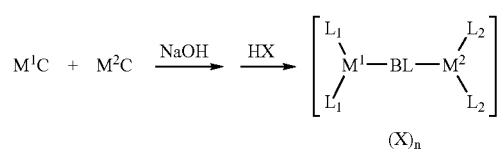

The above metal complex may be used as a metal complex dye, and semiconductor particles sensitized by the metal complex dye can be used to produce a photochemical battery.

A photoelectric conversion element according to the present invention comprises semiconductor particles sensitized by the above metal complex dye. More specifically, semiconductor particles sensitized by the above metal complex dye are fixed on an electrode.

A conductive electrode is preferably a transparent electrode formed on a transparent substrate. Examples of a conducting agent include metals such as gold, silver, copper, platinum and palladium; indium oxide-based compounds, typified by tin-doped indium oxide (ITO); tin oxide-based compounds, typified by fluorine-doped tin oxide (FTO); and zinc oxide-based compounds.

Examples of a semiconductor particle include titanium oxide, zinc oxide, tin oxide and the like. Alternative examples may include indium oxide; niobium oxide; tungsten oxide; vanadium oxide; composite oxide semiconductors such as strontium titanate, calcium titanate, barium titanate and potassium niobate; cadmium or bismuth sulfide; cadmium selenide or telluride; and gallium phosphide or arsenide. The semiconductor particles may be preferably made of an oxide, particularly preferably titanium oxide, zinc oxide or tin oxide or a mixture comprising at least one of these.

A primary particle size of the semiconductor particles is not limited, but is generally 1 to 5,000 nm, preferably 2 to 500 nm, particularly preferably 5 to 300 nm.

A photochemical battery according to the present invention has the above photoelectric conversion element. More specifically, it has the above photoelectric conversion element of the invention and a counter electrode as electrodes and an electrolyte layer between them. At least one of the electrode used in the photoelectric conversion element of the invention and the counter electrode is a transparent electrode.

The counter electrode acts as a cathode when it is combined with the photoelectric conversion element to form a photochemical battery. Although a substrate having a conductive layer may be used as a counter electrode like the above conductive electrode, such a substrate is not necessarily required when a metal plate itself is used. Examples of a conducting agent used in the counter electrode include metals such as platinum and carbon and conductive metal oxides such as fluorine-doped tin oxide.

The electrolyte (oxidation-reduction pair) may be selected from any known materials without limitations. Examples of a usable electrolyte include a combination of iodine and an iodide (for example, metal iodides such as lithium iodide and potassium iodide, or iodides of a quaternary ammonium compound such as tetrabutylammonium iodide, tetrapropylammonium iodide, pyridinium iodide and imidazolium iodide); a combination of bromine and a bromide; a combination of chlorine and a chloride; a combination of an alkylviologen and a reductant thereof; quinone/hydroquinone; transition metal ion pair such as iron (II)/iron (III) ions, copper (I)/copper (II) ions, manganese (II)/manganese (III) ions, and cobalt (II)/cobalt (III) ions; a combination of complex ions such as ferrocyanide/ferricyanide, cobalt (II) tetrachloride/cobalt (III) tetrachloride, cobalt (II) tetrabromide/cobalt (III) tetrabromide, iridium (II) hexachloride/iridium (III) hexachloride, ruthenium (II) hexacyanide/ruthenium (III) hexacyanide, rhodium (II) hexachloride/rhodium (III) hexachloride, rhenium (III) hexachloride/rhenium (IV) hexachloride, rhenium (IV) hexachloride/rhenium (V) hexachloride, osmium (III) hexachloride/osmium (IV) hexachloride, and osmium (IV) hexachloride/osmium (V) hexachloride; a complex formed with a transition metals such as cobalt, iron, ruthenium, manganese, nickel and rhenium, and a conjugated heterocyclic ring and derivative thereof such as bipyridine and derivative thereof, terpyridine and derivative thereof, and phenanthroline and derivative thereof; a complex of cyclopentadiene or derivative thereof and a metal such as ferrocene/ferrocenium ion, cobaltocene/cobaltocenium ion, and ruthenocene/ruthenocenium ion; and porphyrin compounds. A preferable electrolyte is a combination of iodine and lithium iodide or an iodide of a quaternary ammonium compound. The electrolyte may be a solution in an organic solvent, a molten salt, a so-called gel electrolyte in which the electrolyte is impregnated in a polymer matrix, or a solid electrolyte.

A photochemical battery according to the present invention can be produced by any of conventional processes.

For example, on a transparent electrode is applied a semiconductor particle paste such as an oxide, which is then calcined to form a thin film of the semiconductor particles. When the semiconductor-particle thin film is titania, calcination is carried out at a temperature of 450° C. and a reaction time of 30 minutes. This transparent electrode with the thin film is immersed in a dye solution for supporting the dye, to produce a photoelectric conversion element. Then, the photoelectric conversion element is combined with a transparent electrode on which platinum or carbon has been vapor-deposited as a counter electrode, and an electrolyte solution is interposed between them to produce a photochemical battery according to the present invention.

A binuclear metal complex according to the present invention may be also used as a material for an electron transport layer in an organic EL.

EXAMPLES

The present invention will be more specifically described with reference to the following examples. However, the present invention is not limited to these Examples.

For identification of structure, elemental analyses were conducted using YanacoMT-5 (Yanagimoto Mfg. Co., Ltd.) or Micro Coder JM10 (J-SCIENCE LAB Co., Ltd.), and $^1$H-NMR spectra were measured using AL-400 type FT-NMR (JEOL Ltd.).

Example 1

Synthesis of a Binuclear Metal Complex $[(H_2dcbpy)_2Ru(BiIm)Ru(bpy)_2](ClO_4)_2$ (D-1)

1. Synthesis of a Mononuclear Metal Complex $(H_2dcbpy)_2RuCl_2$ ($M^1$C-1)

Under nitrogen atmosphere, in a 500 mL three-necked flask were placed commercially available $RuCl_3.3H_2O$ (2.53 g, 9.68 mmol), $H_2$dcbpy (4.50 g, 18.4 mmol) and 300 mL of N,N-dimethylformamide, and the mixture was refluxed under irradiation with 2.45 GHz microwave for 45 minutes. After cooling down, the mixture was filtered, and the resulting filtrate was evaporated under vacuum to dryness. The resulting residue was washed with acetone/diethyl ether (1:4), 300 mL of 2 mol/L hydrochloric acid was added, and the mixture was stirred with ultrasonic for twenty minutes and then stirred for two hours without ultrasonic. After stirring, an insoluble material was collected by filtration and washed with 2 mol/L hydrochloric acid, acetone/diethyl ether (1:4) and diethyl ether. After drying under vacuum, 5.75 g of $M^1$C-1 was obtained (yield: 85%).

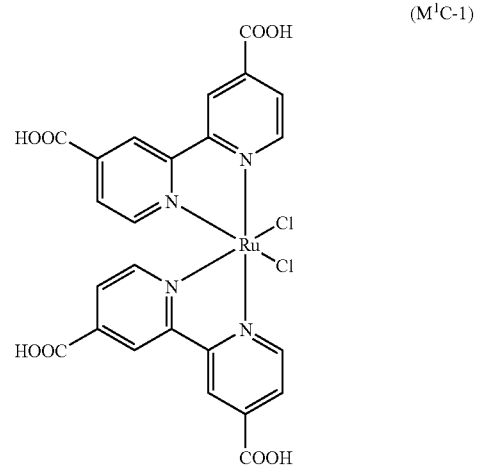

($M^1$C-1)

2. Synthesis of a Mononuclear Metal Complex (BiIm)Ru(bpy)$_2$ ($M^2$C-1)

Under nitrogen atmosphere, in a 100 mL three-necked flask were placed Ru(bpy)$_2$Cl$_2$ (0.501 g, 0.96 mmol) prepared as described in Inorg. Synth., vol. XXIV, 291 (1986), 2,2'-biimidazole (BiImH$_2$) (0.156 g, 1.16 mmol) prepared as described in J. Chem. Soc., 4790 (1961) and 50 mL of ethanol/water (1:1), and the mixture was refluxed under irradiation with 2.45 GHz microwave for 30 minutes. After cooling down, the mixture was filtered, and ethanol in the resulting filtrate was evaporated under vacuum. To the resulting aqueous solution was added an aqueous solution of $NH_4PF_6$ to precipitate a complex as a salt of counter anion $PF_6^-$. After collecting the precipitate by filtration, it was washed with water and recrystallized from methanol. After collecting the precipitated crystals by filtration, they were washed with cold methanol and diethyl ether. After drying under vacuum, 0.575 g of $[(BiImH_2)Ru(bpy)_2](PF_6)_2$ was obtained (yield: 70%).

Subsequently, under nitrogen atmosphere, in a 50 mL Schlenk flask were placed $[(BiImH_2)Ru(bpy)_2](PF_6)_2$ (0.505 g, 0.59 mmol) thus prepared and 30 mL of methanol, and to the mixture was added dropwise 1.48 mL of a 4 mol/L solution of sodium methoxide in methanol. The suspension was refluxed for 30 minutes, and then cooled to room temperature. The insoluble material was collected by filtration, and washed with cold methanol and diethyl ether. After drying under vacuum, 0.251 g of a dark brown powder was obtained.

Next, under nitrogen atmosphere, in a 20 mL Schlenk flask were placed 0.139 g of the dark brown powder thus obtained and 5 mL of methanol, and to the mixture was added 0.5 mL of a 4 mol/L solution of sodium methoxide in methanol, and again refluxed for one hour. After the mixture cooled down, the insoluble material was collected by filtration, and washed with cold methanol and diethyl ether. After drying under vacuum, 96.8 mg of $M^2C$-1 was obtained.

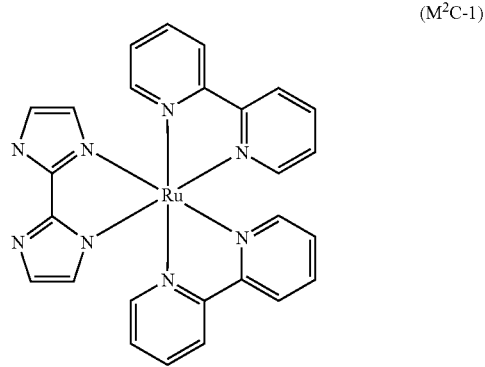

($M^2C$-1)

3. Synthesis of D-1

Under nitrogen atmosphere, in a 100 mL three-necked flask were placed $M^1C$-1 (83.9 mg, 0.12 mmol) and 60 mL of ethanol/water (2:1), and then 0.5 mL of a 1 mol/L aqueous sodium hydroxide solution was added dropwise to give a solution. To the solution was added $M^2C$-1 (78.1 mg, 0.13 mmol), and the mixture was refluxed under irradiation with 2.45 GHz microwave for 15 minutes. After the mixture cooled down, a small amount of the insoluble material was removed by filtration, and ethanol in the filtrate was evaporated under vacuum. To the resulting aqueous solution was added dropwise a 0.5 mol/L aqueous perchloric acid solution to pH 2.5. The precipitated complex was collected by filtration, and washed with an aqueous perchloric acid solution at pH 2.5, acetone/diethyl ether (4:1) and diethyl ether. After drying under vacuum, 0.110 g of D-1 was obtained (yield: 66%). The elemental analysis results were in good agreement with the values of a trihydrate.

Figure 1:
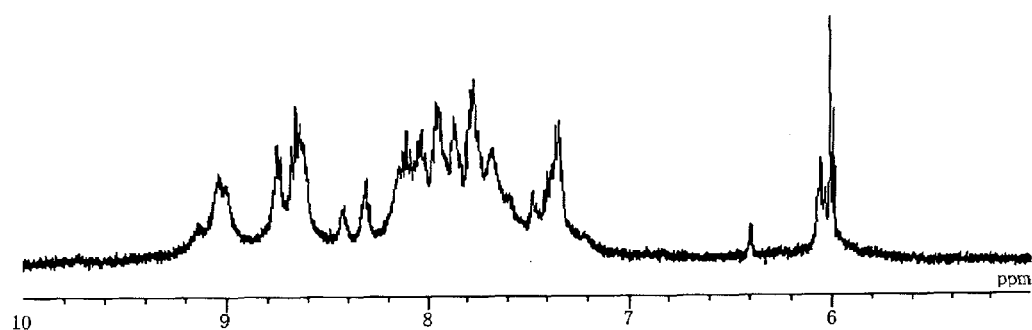
FIG. 1 shows a $^1$H-NMR spectrum of the binuclear metal complex (D-1) prepared in Example 1 according to the present invention in dimethyl sulfoxide-d6.

Elemental Analysis
  Observed: C:43.50, H:3.50, N:12.30
  Calculated: C:43.30, H:3.10, N:12.10.
  $^1$H-NMR spectrum of the complex is shown in FIG. 1.

Example 2

Synthesis of a Binuclear Metal Complex $[(H_2dcbpy)(Hdcbpy)Ru(BiIm)Ru(bpy)_2](PF_6)$ (D-2)

Under nitrogen atmosphere, in a 100 mL three-necked flask were placed $M^1C$-1 (62.4 mg, 0.090 mmol) and 30 mL of ethanol/water (1:1), and 0.4 mL of a 1 mol/L aqueous sodium hydroxide solution was added dropwise to give a solution. To the solution was added $M^2C$-1 (58.4 mg, 0.097 mmol), and the mixture was refluxed under irradiation with 2.45 GHz microwave for 15 minutes. After cooling down, the mixture was filtered and ethanol in the filtrate was evaporated under vacuum. To the resulting aqueous solution was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 49.3 mg of D-2 was obtained (yield: 41%). The elemental analysis results were in good agreement with the values of a tetrahydrate.

Figure 2:
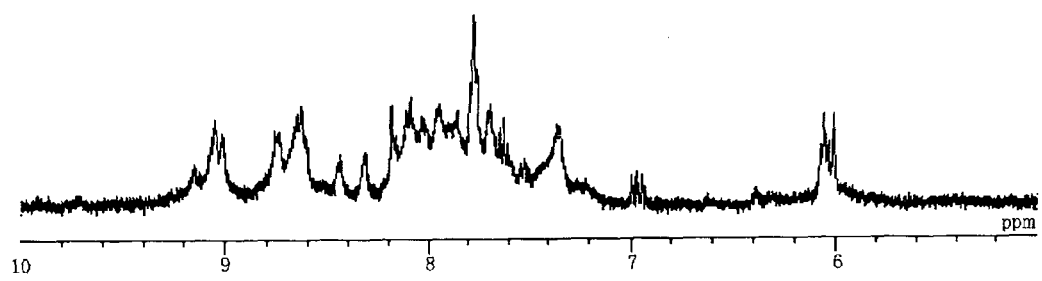
FIG. 2 shows a $^1$H-NMR spectrum of the binuclear metal complex (D-2) prepared in Example 2 according to the present invention in dimethyl sulfoxide-d6.

Elemental Analysis
  Observed: C:44.60, H:3.50, N:12.60
  Calculated: C:44.50, H:3.20, N:12.40.
  $^1$H-NMR spectrum of the complex is shown in FIG. 2.

Example 3

Synthesis of a Binuclear Metal Complex $[(H_2dcbiq)(Hdcbiq)Ru(BiIm)Ru(bpy)_2](PF_6)$ (D-3)

1. Synthesis of a Mononuclear Metal Complex $(H_2dcbiq)_2RuCl_2$ ($M^1C$-2)

Under nitrogen atmosphere, in a 100 mL three-necked flask were placed $RuCl_2(DMSO)_4$ (0.468 g, 0.97 mmol) prepared as described in J. Chem. Soc., Dalton Trans. 204 (1973), commercially available $K_2dcbiq$ (0.91 g, 1.92 mmol) and 40 mL of ethylene glycol, and the mixture was refluxed under irradiation with 2.45 GHz microwave for 3 minutes. After cooling down, the mixture was filtered, and to the resulting filtrate was added dropwise 0.1 mol/L nitric acid to pH 2.5. The precipitated complex was collected by filtration, and washed with nitric acid at pH 2.5, acetone/diethyl ether (4:1) and diethyl ether. After drying under vacuum, 0.72 g of $M^1C$-2 was obtained (yield: 83%).

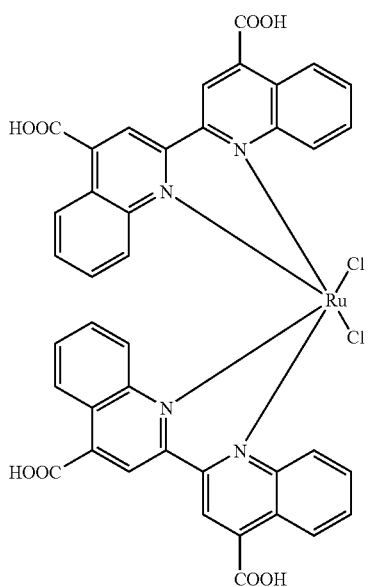

(M¹C-2)

2. Synthesis of D-3

Under nitrogen atmosphere, in a 100 mL three-necked flask were placed M¹C-2 (96.0 mg, 0.11 mmol) and 100 mL of ethanol/water (1:1), and then 0.45 mL of a 1 mol/L aqueous sodium hydroxide solution was added dropwise to give a solution. To the solution was added M²C-1 (70.8 mg, 0.12 mmol), and the mixture was refluxed under irradiation with 2.45 GHz microwave for 15 minutes. After cooling down, the mixture was filtered, and ethanol in the filtrate was evaporated under vacuum. The resulting suspension was filtered, and to the filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 95.2 mg of D-3 was obtained (yield: 60%). The elemental analysis results were in good agreement with the values of an anhydride.

Elemental Analysis

Observed: C:54.30, H:3.20, N:11.40

Calculated: C:53.59, H:2.93, N:11.36.

Figure 3:
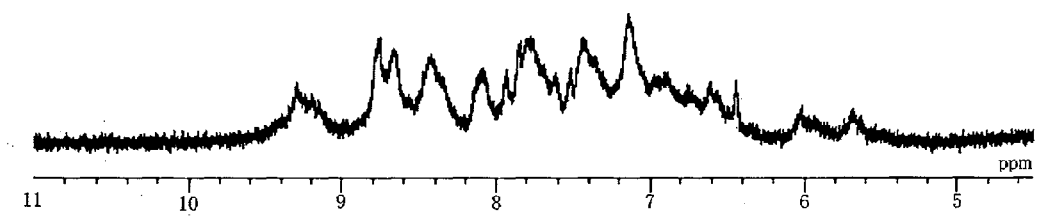
FIG. 3 shows a $^1$H-NMR spectrum of the binuclear metal complex (D-3) prepared in Example 3 according to the present invention in dimethyl sulfoxide-d6.

¹H-NMR spectrum of the complex is shown in FIG. 3.

Example 4

Synthesis of a Binuclear Metal Complex

[(H₂dcbpy)(Hdcbpy)Ru(BiBzIm)Ru(bpy)₂](PF₆)
(D-4)

1. Synthesis of a Mononuclear Metal Complex (BiBzIm)Ru(bpy)₂ (M²C-2)

Under nitrogen atmosphere, in a 100 mL three-necked flask were placed Ru(bpy)₂Cl₂ (0.505 g, 0.97 mmol), 2,2'-bibenzimidazole (BiBzImH₂) (0.343 g, 1.46 mmol) prepared as described in Inorg. Chem., 34, 5979 (1995) and 20 mL of ethylene glycol, and the mixture was refluxed under irradiation with 2.45 GHz microwave for 5 minutes. After the mixture cooled down, 20 mL of water was added to precipitate the unreacted bibenzimidazole. After filtration, to the resulting filtrate was added an aqueous solution of NH₄PF₆ to precipitate a complex as a salt of counter anion PF₆⁻. The precipitate was collected by filtration, and then washed with water and recrystallized from methanol. After collecting the precipitated crystals by filtration, they were washed with cold methanol and diethyl ether. After drying under vacuum, 0.905 g of [(BiBzImH₂)Ru(bpy)₂](PF₆)₂ was obtained (yield: 96%).

Subsequently, under nitrogen atmosphere, in a 50 mL Schlenk flask were placed [(BiBzImH₂)Ru(bpy)₂](PF₆)₂ (0.877 g, 0.90 mmol) thus prepared and 30 mL of methanol, and to the mixture was added dropwise 1.8 mL of a 28% solution of sodium methoxide in methanol. The suspension was refluxed for one hour, and then cooled to room temperature. The insoluble material was collected by filtration, and washed with water, cold methanol and diethyl ether. After drying under vacuum, 0.587 g of M²C-2 was obtained (yield: 96%).

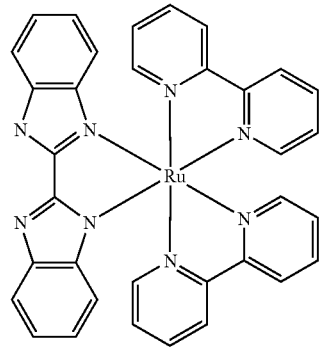

(M²C-2)

2. Synthesis of D-4

Under nitrogen atmosphere, in a 300 mL three-necked flask were placed M¹C-1 (0.509 g, 0.73 mmol) and 100 mL of ethanol/water (1:1), and then 3.2 mL of a 1 mol/L aqueous sodium hydroxide solution was added dropwise to give a solution. To the solution was added M²C-2 (0.522 g, 0.77 mmol), and the mixture was refluxed under irradiation with 2.45 GHz microwave for 30 minutes. After the mixture cooled down, a small amount of the insoluble material was removed by filtration, and ethanol in the filtrate was evaporated under vacuum. The resulting suspension was filtered, and to the filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 0.873 g of D-4 was obtained (yield: 85%). The elemental analysis results were in good agreement with the values of a dihydrate.

Elemental Analysis

Observed: C:49.07, H:3.29, N:11.89

Calculated: C:49.23, H:3.06, N:11.88.

Figure 4:
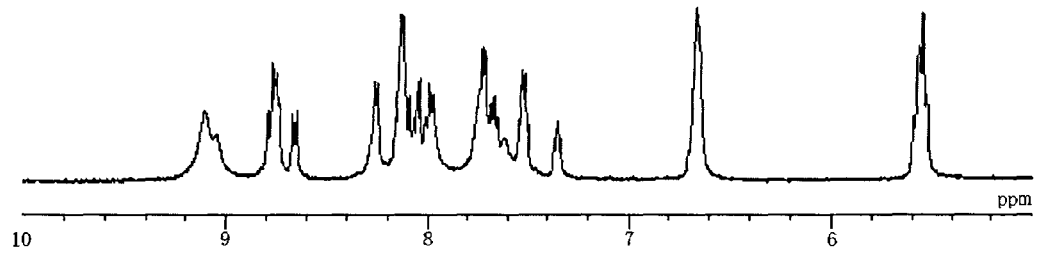
FIG. 4 shows a $^1$H-NMR spectrum of the binuclear metal complex (D-4) prepared in Example 4 according to the present invention in dimethyl sulfoxide-d6.
Figure 5:
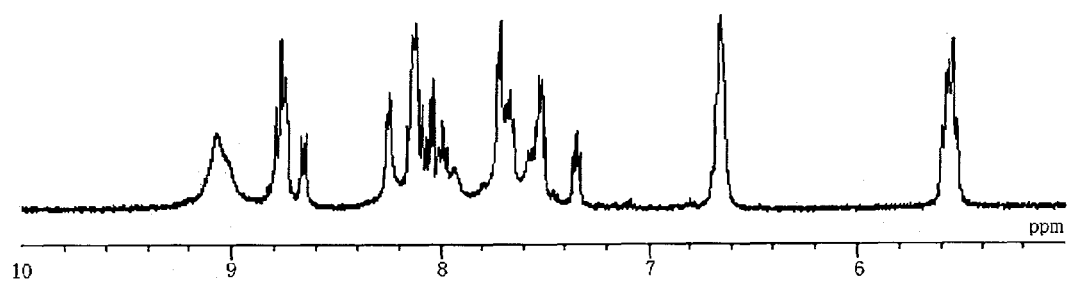
FIG. 5 shows a $^1$H-NMR spectrum of the binuclear metal complex (D-5) prepared in Example 5 according to the present invention in dimethyl sulfoxide-d6.
Figure 6:
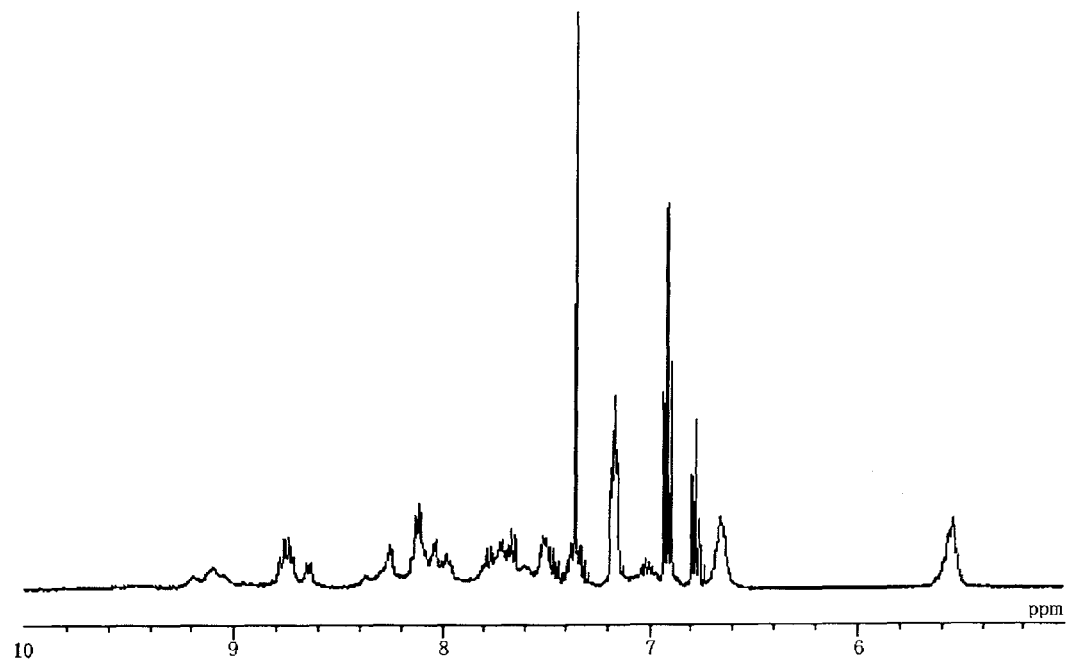
FIG. 6 shows a $^1$H-NMR spectrum of the binuclear metal complex (D-6) prepared in Example 5 according to the present invention in dimethyl sulfoxide-d6.
Figure 7:
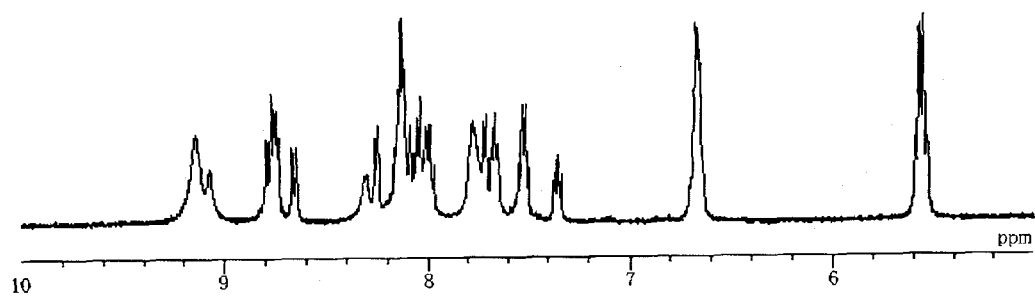
FIG. 7 shows a $^1$H-NMR spectrum of the binuclear metal complex (D-7) prepared in Example 5 according to the present invention in dimethyl sulfoxide-d6.
Figure 8:
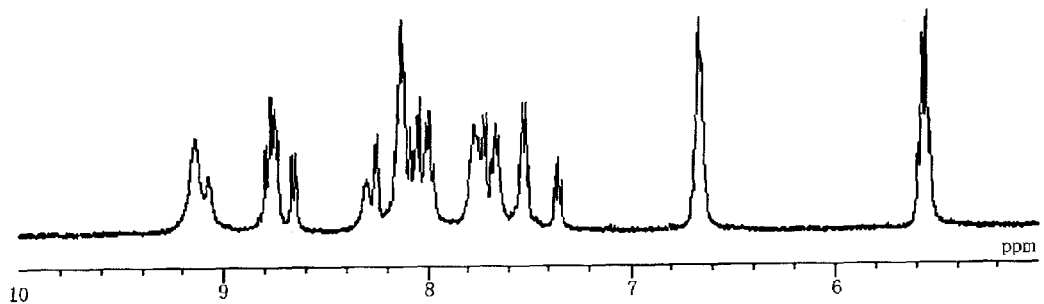
FIG. 8 shows a $^1$H-NMR spectrum of the binuclear metal complex (D-8) prepared in Example 5 according to the present invention in dimethyl sulfoxide-d6.
Figure 9:
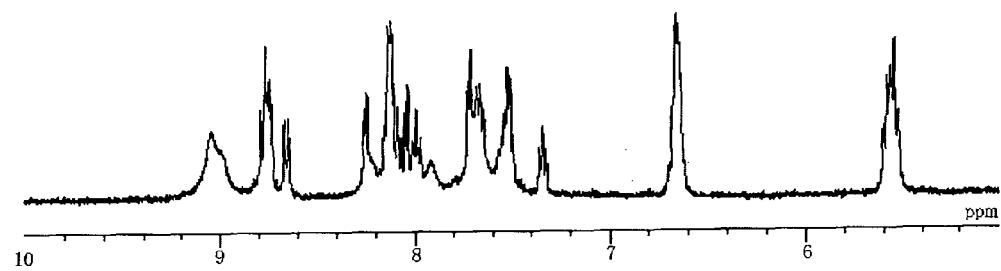
FIG. 9 shows a $^1$H-NMR spectrum of the binuclear metal complex (D-9) prepared in Example 5 according to the present invention in dimethyl sulfoxide-d6.
Figure 10:
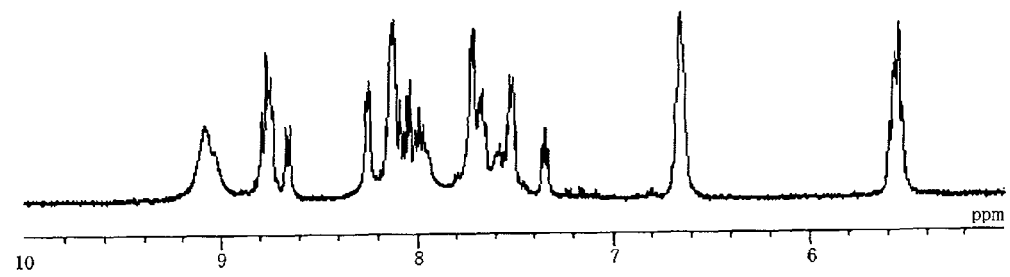
FIG. 10 shows a $^1$H-NMR spectrum of the binuclear metal complex (D-10) prepared in Example 5 according to the present invention in dimethyl sulfoxide-d6.

¹H-NMR spectrum of the complex is shown in FIG. 4.

Example 5

Synthesis of D-5, D-6, D-7 D-8, D-9 and D-10

D-5, D-7, D-8, D-9 and D-10 were prepared as described in the synthetic process for D-4 in Example 4, substituting an acid corresponding to a counter anion for a 0.5 mol/L aqueous hexafluorophosphoric acid solution and an aqueous hexafluorophosphoric acid solution at pH 2.5, respectively. Since D-6 does not have any corresponding acid, it was prepared by using a 0.5 mol/L aqueous hydrochloric acid solution and an aqueous hydrochloric acid solution at pH 2.5, and adding sodium tetraphenylborate in a molar amount 10 times as much as $M^1C$-1 before adding dropwise the 0.5 mol/L aqueous hydrochloric acid solution. The structures of D-5, D-6, D-7, D-8, D-9 and D-10 were also identified by elemental analysis and $^1$H-NMR spectrometry.

The elemental analysis results for D-5 were in good agreement with the values of a trihydrate.

Elemental Analysis
  Observed: C:50.66, H:3.26, N:12.18
  Calculated: C:50.66, H:3.30, N:12.22.
  The elemental analysis results for D-6 were in good agreement with the values of a tetrahydrate.

Elemental Analysis
  Observed: C:60.15, H:3.81, N:10.34
  Calculated: C:60.59, H:4.15, N:10.34.
  The elemental analysis results for D-7 were in good agreement with the values of a tetrahydrate.

Elemental Analysis
  Observed: C:48.87, H:3.04, N:11.60
  Calculated: C:48.69, H:3.26, N:11.55.
  The elemental analysis results for D-8 were in good agreement with the values of a tetrahydrate.

Elemental Analysis
  Observed: C:49.40, H:3.10, N:11.85
  Calculated: C:49.56, H:3.37, N:11.96.
  The elemental analysis results for D-9 were in good agreement with the values of a hexahydrate.

Elemental Analysis
  Observed: C:49.46, H:3.34, N:12.41
  Calculated: C:49.61, H:3.66, N:12.97.
  The elemental analysis results for D-10 were in good agreement with the values of a dihydrate.

Elemental Analysis
  Observed: C:49.70, H:3.23, N:11.89
  Calculated: C:49.86, H:3.10, N:12.03.
  $^1$H-NMR spectra for D-5, D-6, D-7, D-8, D-9 and D-10 are shown in FIGS. 5, 6, 7, 8, 9 and 10, respectively.

Example 6

Synthesis of a Binuclear Metal Complex

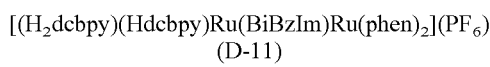
(D-11)

1. Synthesis of a Mononuclear Metal Complex (BiBzIm)Ru(phen)$_2$ (M$^2$C-3)

Under nitrogen atmosphere, in a 100 mL three-necked flask were placed Ru(phen)$_2$Cl$_2$ (0.509 g, 0.90 mmol) prepared as described in Inorg. Synth., vol. XXIV, 291 (1986), 2,2'-bibenzimidazole (BiBzImH$_2$) (0.252 g, 1.08 mmol) and 50 mL of ethanol/water (1:1), and the mixture was refluxed under irradiation with 2.45 GHz microwave for 30 minutes. After cooling down, the mixture was filtered, and ethanol in the resulting filtrate was evaporated under vacuum. The resulting suspension was filtered, and to the filtrate was added an aqueous solution of NH$_4$PF$_6$ to precipitate a complex as a salt of counter anion PF$_6^-$. The precipitate was collected by filtration, and then washed with water and recrystallized from methanol. After collecting the precipitated crystals by filtration, they were washed with cold methanol and diethyl ether. After drying under vacuum, 0.545 g of [(BiBzImH$_2$)Ru(phen)$_2$](PF$_6$)$_2$ was obtained (yield: 62%).

Subsequently, under nitrogen atmosphere, in a 50 mL Schlenk flask were placed [(BiBzImH$_2$)Ru(phen)$_2$](PF$_6$)$_2$ (0.483 g, 0.49 mmol) thus prepared and 20 mL of methanol, and to the mixture was added dropwise 0.95 mL of a 28% solution of sodium methoxide in methanol. The suspension was refluxed for one hour, and then cooled to room temperature. The insoluble material was collected by filtration, and washed with cold methanol, water and diethyl ether. After drying under vacuum, 0.334 g of M$^2$C-3 was obtained (yield: 91%).

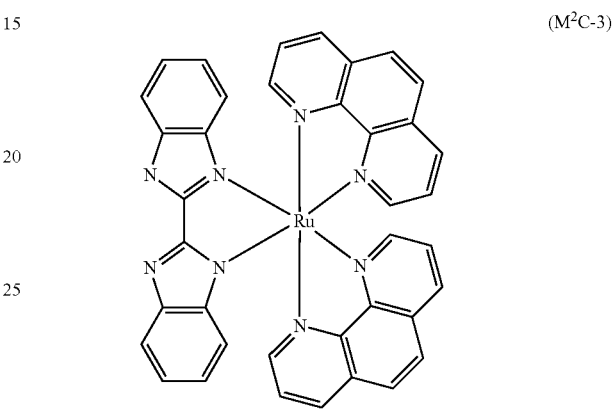
(M$^2$C-3)

2. Synthesis of D-11

Under nitrogen atmosphere, in a 100 mL three-necked flask were placed M$^1$C-1 (0.106 g, 0.15 mmol) and 60 mL of ethanol/water (2:1), and 0.61 mL of a 1 mol/L aqueous sodium hydroxide solution was added dropwise to give a solution. To the solution was added M$^2$C-3 (0.114 g, 0.15 mmol), and the mixture was refluxed under irradiation with 2.45 GHz microwave for 15 minutes. After the mixture cooled down, a small amount of the insoluble material was removed by filtration, and ethanol in the filtrate was evaporated under vacuum. The resulting suspension was filtered, and to the filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 0.173 g of D-11 was obtained (yield: 76%). The elemental analysis results were in good agreement with the values of a tetrahydrate.

Figure 11:
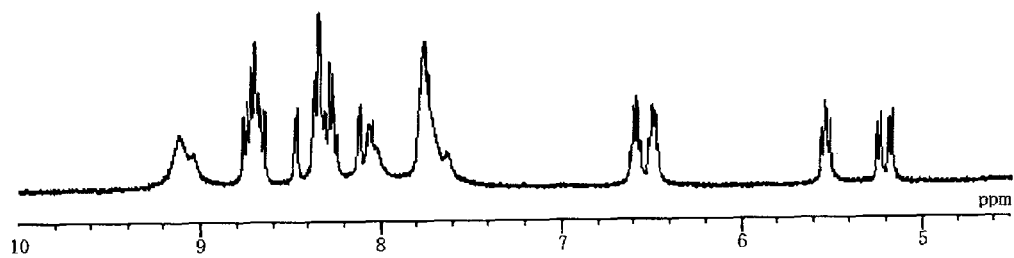
FIG. 11 shows a $^1$H-NMR spectrum of the binuclear metal complex (D-11) prepared in Example 6 according to the present invention in dimethyl sulfoxide-d6.

Elemental Analysis
  Observed: C:49.60, H:3.10, N:11.20
  Calculated: C:49.67, H:3.16, N:11.21.
  $^1$H-NMR spectrum of the complex is shown in FIG. 11.

Example 7

Synthesis of a Binuclear Metal Complex

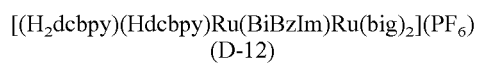
(D-12)

1. Synthesis of a Mononuclear Metal Complex (BiBzIm)Ru(biq)$_2$ (M$^2$C-4)

Under nitrogen atmosphere, in a 100 mL three-necked flask were placed Ru(biq)$_2$Cl$_2$ (0.228 g, 0.33 mmol) prepared as described in Inorg. Synth., vol. XXIV, 291 (1986), 2,2'-bibenzimidazole (BiBzImH$_2$) (0.153 g, 0.65 mmol) and 10 mL of ethylene glycol, and the mixture was refluxed under irradiation with 2.45 GHz microwave for 5 minutes. After the mixture cooled down, 10 mL of water was added to precipitate the unreacted bibenzimidazole. After filtration, to the resulting filtrate was added an aqueous solution of NH$_4$PF$_6$ to precipitate a complex as a salt of counter anion PF$_6^-$. The precipitate was collected by filtration, and washed with water and diethyl ether. After drying under vacuum, 0.242 g of [(BiBzImH$_2$)Ru(biq)$_2$](PF$_6$)$_2$ was obtained (yield: 64%).

Subsequently, under nitrogen atmosphere, in a 20 mL Schlenk flask were placed [(BiBzImH$_2$)Ru(phen)$_2$](PF$_6$)$_2$ (0.205 g, 0.18 mmol) thus prepared and 20 mL of methanol, and to the mixture was added dropwise 0.43 mL of a 28% solution of sodium methoxide in methanol. The suspension was refluxed for 1.5 hours, and then cooled to room temperature. The insoluble material was collected by filtration, and washed with cold methanol, water and diethyl ether. After drying under vacuum, 0.140 g of M$^2$C-4 was obtained (yield: 81%).

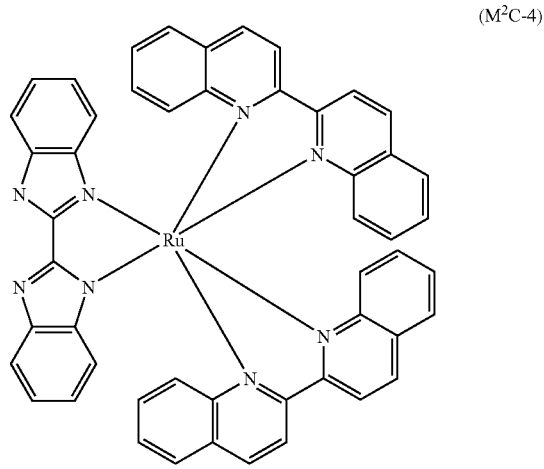

(M$^2$C-4)

2. Synthesis of D-12

Under nitrogen atmosphere, in a 100 mL three-necked flask were placed M$^1$C-1 (75.4 mg, 0.11 mmol) and 40 mL of N,N-dimethylformamide/water (3:1), and then 0.45 mL of a 1 mol/L aqueous sodium hydroxide solution was added dropwise to give a solution. To the solution was added M$^2$C-4 (0.114 g, 0.12 mmol), and the mixture was refluxed under irradiation with 2.45 GHz microwave for 15 minutes. After cooling down, the mixture was filtered, and the resulting filtrate was evaporated under vacuum to dryness. To the resulting residue was added 30 mL of water, and the insoluble material was removed by filtration. To the resulting filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 0.143 g of D-12 was obtained (yield: 82%). The elemental analysis results were in good agreement with the values of a dihydrate.

Figure 12:
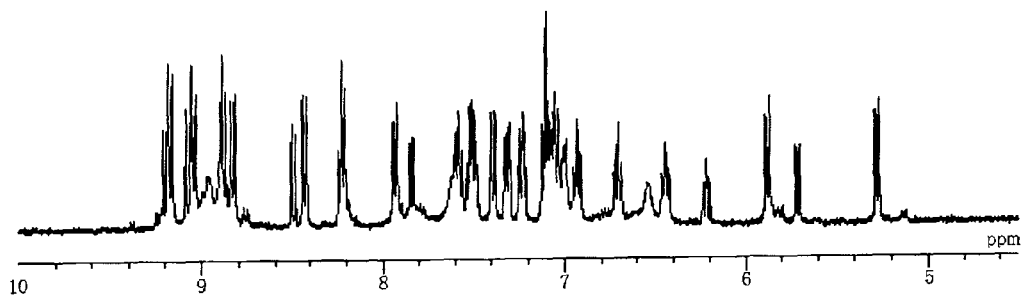
FIG. 12 shows a $^1$H-NMR spectrum of the binuclear metal complex (D-12) prepared in Example 7 according to the present invention in dimethyl sulfoxide-d6.

Elemental Analysis
Observed: C:55.00, H:3.40, N:10.50
Calculated: C:55.02, H:3.18, N:10.41.
$^1$H-NMR spectrum of the complex is shown in FIG. 12.

Example 8

Synthesis of a Binuclear Metal Complex

[(H$_2$dcbpy)(Hdcbpy)Ru(BiBzIm)Ru(dmbpy)$_2$](PF$_6$)
(D-13)

1. Synthesis of a Mononuclear Metal Complex (BiBzIm)Ru(dmbpy)$_2$ (M$^2$C-5)

Under nitrogen atmosphere, in a 100 mL three-necked flask were placed Ru(dmbpy)$_2$Cl$_2$ (1.00 g, 1.79 mmol) prepared as described in Inorg. Synth., vol. XXIV, 291 (1986), 2,2'-bibenzimidazole (BiBzImH$_2$) (0.49 g, 2.09 mmol) and 40 mL of ethylene glycol, and the mixture was refluxed under irradiation with 2.45 GHz microwave for 5 minutes. After the mixture cooled down, 40 mL of water was added to precipitate the unreacted bibenzimidazole. After filtration, to the resulting filtrate was added an aqueous solution of NH$_4$PF$_6$ to precipitate a complex as a salt of counter anion PF$_6^-$. The precipitate was collected by filtration, and washed with water and diethyl ether. After drying under vacuum, 1.58 g of [(BiBzImH$_2$)Ru(dmbpy)$_2$](PF$_6$)$_2$ was obtained (yield: 89%).

Subsequently, under nitrogen atmosphere, in a 50 mL Schlenk flask were placed [(BiBzImH$_2$)Ru(dmbpy)$_2$](PF$_6$)$_2$ (1.00 g, 1.01 mmol) thus prepared and 30 mL of methanol, and to the mixture was added dropwise 1.9 mL of a 28% solution of sodium methoxide in methanol. The suspension was refluxed for one hour, and then cooled to room temperature. The insoluble material was collected by filtration, and washed with cold methanol, water and diethyl ether. After drying under vacuum, 0.74 g of M$^2$C-5 was obtained (yield: 95%).

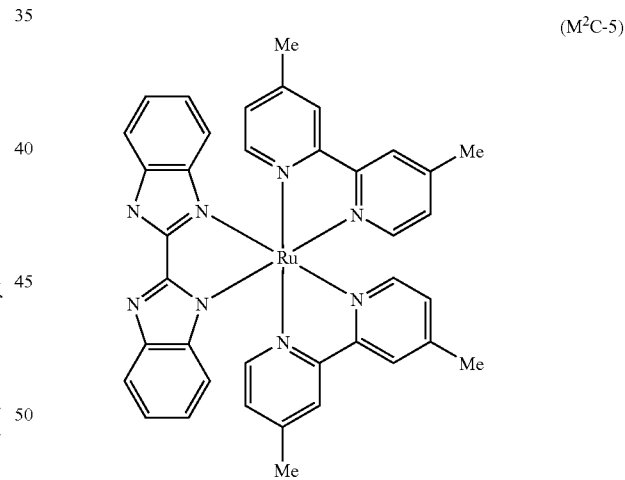

(M$^2$C-5)

2. Synthesis of D-13

Under nitrogen atmosphere, in a 100 mL three-necked flask were placed M$^1$C-1 (0.204 g, 0.29 mmol) and 50 mL of ethanol/water (1:1), and then 1.2 mL of a 1 mol/L aqueous sodium hydroxide solution was added dropwise to give a solution. To the solution was added M$^2$C-5 (0.228 g, 0.29 mmol), and the mixture was refluxed under irradiation with 2.45 GHz microwave for 15 minutes. After cooling down, the mixture was filtered, and ethanol in the filtrate was evaporated under vacuum. The resulting suspension was filtered, and to the filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 0.366 g of D-13 was obtained (yield: 87%). The elemental analysis results were in good agreement with the values of an anhydride.

Figure 13:
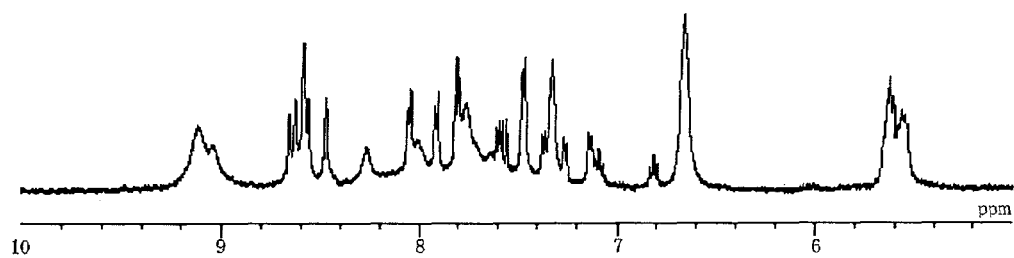
FIG. 13 shows a $^1$H-NMR spectrum of the binuclear metal complex (D-13) prepared in Example 8 according to the present invention in dimethyl sulfoxide-d6.

Elemental Analysis
Observed: C:51.80, H:3.40, N:11.50
Calculated: C:51.89, H:3.30, N: 11.71.
$^1$H-NMR spectrum of the complex is shown in FIG. 13.

Example 9

Synthesis of a Binuclear Metal Complex

[(H$_2$dcbpy)(Hdcbpy)Ru(TMBiBzIm)Ru(bpy)$_2$](PF$_6$) (D-14)

1. Synthesis of a Mononuclear Metal Complex (TMBiBzIm)Ru(bpy)$_2$ (M$^2$C-6)

Under nitrogen atmosphere, in a 100 mL three-necked flask were placed Ru(bpy)$_2$Cl$_2$ (0.508 g, 0.98 mmol), 5,6,5', 6'-tetramethyl-2,2'-bibenzimidazole (TMBiBzImH$_2$) (0.343 g, 1.18 mmol) prepared as described in Inorg. Chem., 34, 5981-5982 (1995) and 20 mL of ethylene glycol, and the mixture was refluxed under irradiation with 2.45 GHz microwave for 5 minutes. After the mixture cooled down, 20 mL of water was added to precipitate the unreacted TMBiBzImH$_2$. After filtration, to the resulting filtrate was added an aqueous solution of NH$_4$PF$_6$ to precipitate a complex as a salt of counter anion PF$_6^-$. The precipitate was collected by filtration, and washed with water and diethyl ether. After drying under vacuum, 0.969 g of [(TMBiBzImH$_2$)Ru(bpy)$_2$](PF$_6$)$_2$ was obtained (yield: 99%).

Subsequently, under nitrogen atmosphere, in a 50 mL Schlenk flask were placed [(TMBiBzImH$_2$)Ru(bpy)$_2$](PF$_6$)$_2$ (0.93 g, 0.93 mmol) thus prepared and 30 mL of methanol, and to the mixture was added dropwise 1.9 mL of a 28% solution of sodium methoxide in methanol. The suspension was refluxed for one hour, and then cooled to room temperature. The insoluble material was collected by filtration, and washed with cold methanol, water and diethyl ether. After drying under vacuum, 0.58 g of M$^2$C-6 was obtained (yield: 81%).

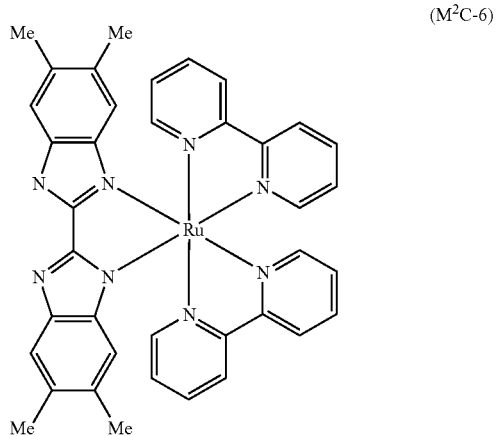

(M$^2$C-6)

2. Synthesis of D-14

Under nitrogen atmosphere, in a 100 mL three-necked flask were placed M$^1$C-1 (0.102 g, 0.15 mmol) and 60 mL of N,N-dimethylformamide/water (5:1), and then 0.62 mL of a 1 mol/L aqueous sodium hydroxide solution was added dropwise to give a solution. To the solution was added M$^2$C-6 (0.115 g, 0.16 mmol), and the mixture was refluxed under irradiation with 2.45 GHz microwave for 25 minutes. After cooling down, the mixture was filtered, and the resulting filtrate was evaporated under vacuum to dryness. To the resulting residue was added 50 mL of water, and the insoluble material was removed by filtration. To the resulting filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 0.145 g of D-14 was obtained (yield: 67%). The elemental analysis results were in good agreement with the values of a dihydrate.

Figure 14:
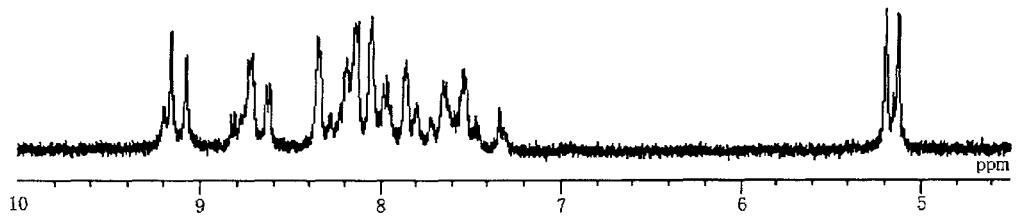
FIG. 14 shows a $^1$H-NMR spectrum of the binuclear metal complex (D-14) prepared in Example 9 according to the present invention in dimethyl sulfoxide-d6.

Elemental Analysis
Observed: C:50.62, H:3.53, N:11.35
Calculated: C:50.61, H:3.49, N:11.42.
$^1$H-NMR spectrum of the complex is shown in FIG. 14.

Example 10

Synthesis of a Binuclear Metal Complex

[(H$_2$dcbpy)(Hdcbpy)Ru(BiBzIm)Os(bpy)$_2$](PF$_6$) (D-15)

1. Synthesis of a Mononuclear Metal Complex (BiBzIm)Os(bpy)$_2$ (M$^2$C-7)

Under nitrogen atmosphere, in a 100 mL three-necked flask were placed Os(bpy)$_2$Cl$_2$ (0.501 g, 0.87 mmol) prepared as described in Inorg. Chem., 27, 3195 (1988), BiBzImH$_2$ (0.613 g, 2.62 mmol) and 20 mL of ethylene glycol, and the mixture was refluxed under irradiation with 2.45 GHz microwave for 5 minutes. After the mixture cooled down, 20 mL of water was added to precipitate the unreacted BiBzImH$_2$. After filtration, to the resulting filtrate was added an aqueous solution of NH$_4$PF$_6$ to precipitate a complex as a salt of counter anion PF$_6^-$. The precipitate was collected by filtration, and washed with water and diethyl ether. After drying under vacuum, 0.790 g of [(BiBzImH$_2$)Os(bpy)$_2$](PF$_6$)$_2$ was obtained (yield: 87%).

Subsequently, under nitrogen atmosphere, in a 50 mL Schlenk flask were placed [(BiBzImH$_2$)Os(bpy)$_2$](PF$_6$)$_2$ (0.77 g, 0.74 mmol) thus prepared and 30 mL of methanol, and to the mixture was added dropwise 1.45 mL of a 28% solution of sodium methoxide in methanol. The suspension was refluxed for one hour, and then cooled to room temperature. The insoluble material was collected by filtration, and washed with cold methanol, water and diethyl ether. After drying under vacuum, 0.51 g of M$^2$C-7 was obtained (yield: 89%).

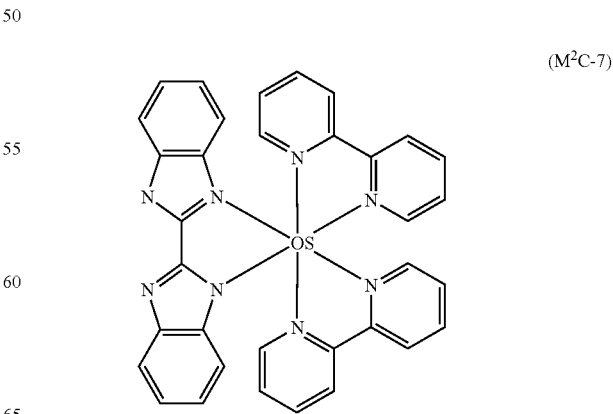

(M$^2$C-7)

2. Synthesis of D-15

Under nitrogen atmosphere, in a 100 mL three-necked flask were placed M$^1$C-1 (0.101 g, 0.15 mmol) and 40 mL of N,N-dimethylformamide/water (3:1), and then 0.61 mL of a 1 mol/L aqueous sodium hydroxide solution was added dropwise to give a solution. To the solution was added M$^2$C-7 (0.168 g, 0.22 mmol), and the mixture was refluxed under irradiation with 2.45 GHz microwave for 15 minutes. After cooling down, the mixture was filtered, and the resulting filtrate was evaporated under vacuum to dryness. To the resulting residue was added 30 mL of water, and the insoluble material was removed by filtration. To the resulting filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 0.172 g of D-15 was obtained (yield: 79%). The elemental analysis results were in good agreement with the values of a dihydrate.

Figure 15:
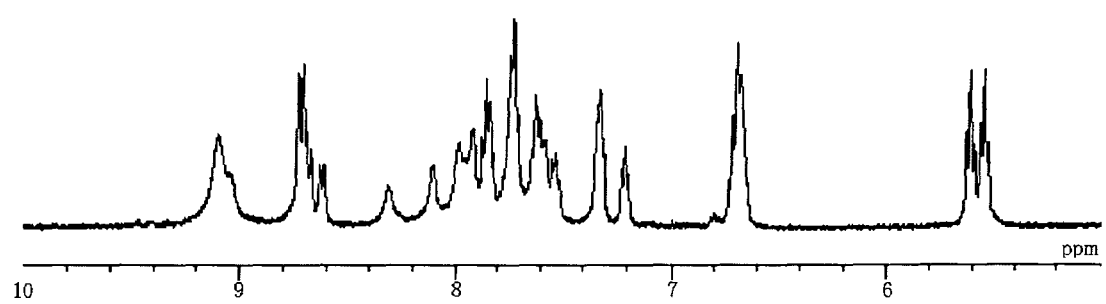
FIG. 15 shows a $^1$H-NMR spectrum of the binuclear metal complex (D-15) prepared in Example 10 according to the present invention in dimethyl sulfoxide-d6.
Figure 16:
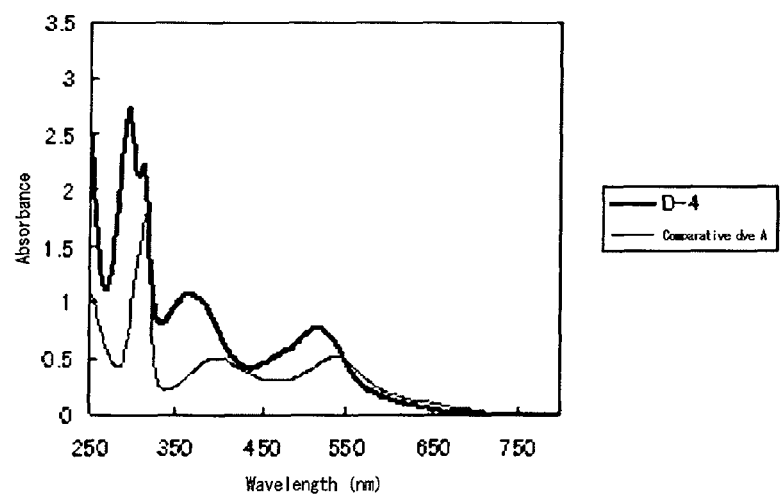
FIG. 16 shows a comparison of UV-visible absorption spectra of the binuclear metal complex dye (D-4) prepared in Example 4 and Comparative dye A.
Figure 17:
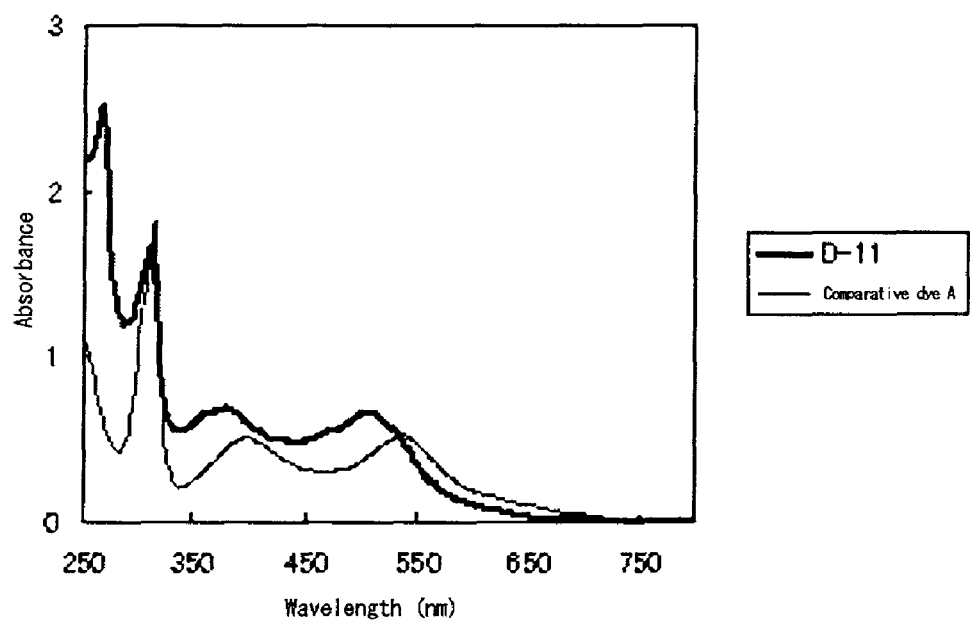
FIG. 17 shows a comparison of UV-visible absorption spectra of the binuclear metal complex dye (D-11) prepared in Example 6 and Comparative dye A.
Figure 18:
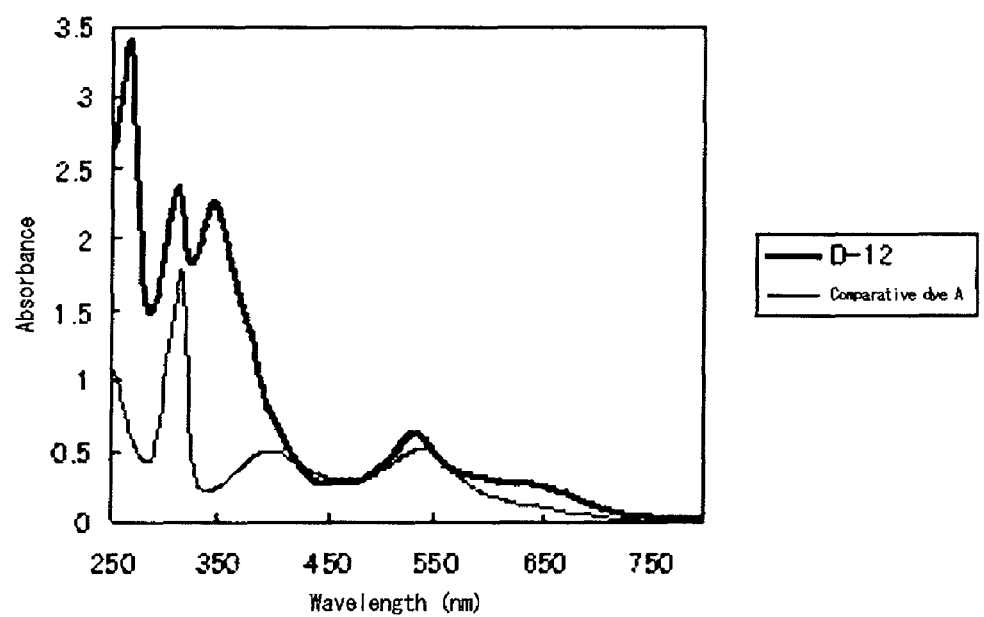
FIG. 18 shows a comparison of UV-visible absorption spectra of the binuclear metal complex dye (D-12) prepared in Example 7 and Comparative dye A.
Figure 19:
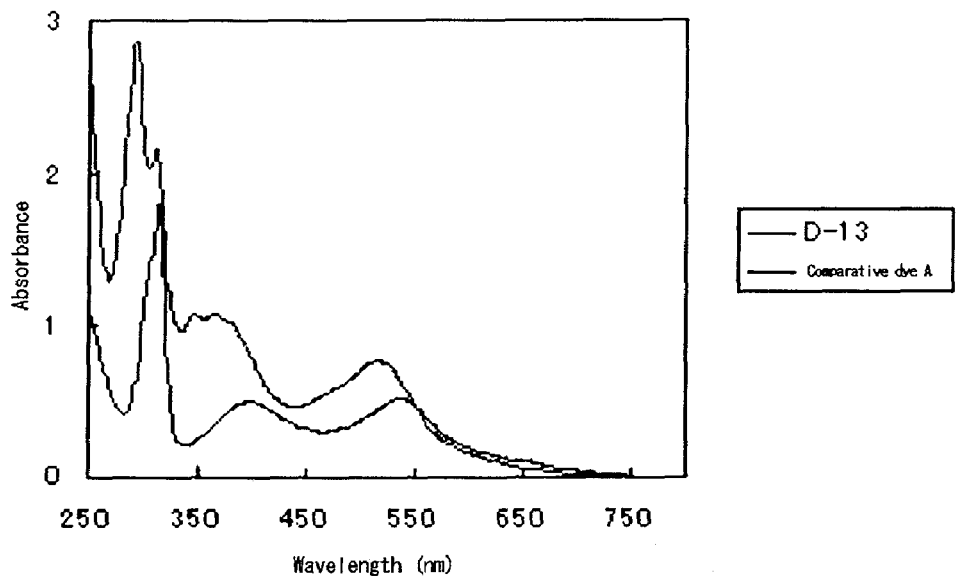
FIG. 19 shows a comparison of UV-visible absorption spectra of the binuclear metal complex dye (D-13) prepared in Example 8 and Comparative dye A.

Elemental Analysis
Observed: C:46.80, H:3.30, N:10.90
Calculated: C:46.31, H:2.88, N:11.17.
$^1$H-NMR spectrum of the complex is shown in FIG. 15.

Example 11

Absorption Spectral Measurement

For each of D-4, D-11, D-12, D-13 and the following Comparative dye A as an existing mononuclear metal complex dye (N3dye, a ruthenium organic complex from Kojima Chemicals Co., Ltd.), an ethanol solution was prepared at a concentration of 3×10$^{-5}$ mol/L, and was subjected to measurement using a UV-visible absorption spectrum at a wavelength of 250 nm to 800 nm (JASCO Corporation, V-570). The results are shown in FIGS. 16, 17, 18 and 19.

Comparative Dye A

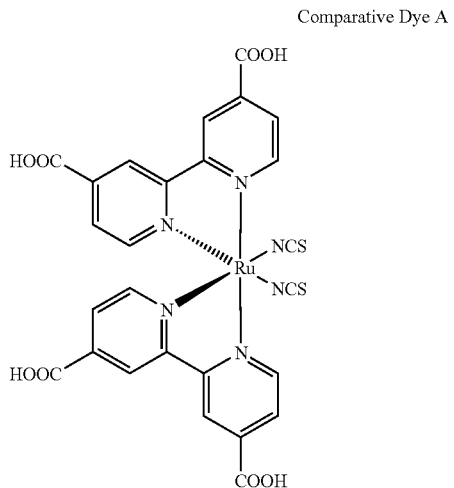

As seen from FIGS. 16, 17, 18 and 19, all of the binuclear metal complex dyes of the present invention have an absorption wavelength range similar to that of Comparative dye A as an existing dye exhibiting a high photoelectric conversion efficiency, and have a further higher absorbance index. It is, therefore, very preferable to use a binuclear metal complex dye of the present invention in a photochemical battery because it absorbs more light to be converted into a photocurrent.

Example 12

1. Preparation of a Porous Titania Electrode

Preparation of a Porous Titania Electrode (T-1)

To 5.0 g of a 30 wt % titania microparticle dispersed slurry (Titan Kogyo KK., 20 nm microparticles) were added 0.2 mL of acetylacetone, 1 mL of a 2 wt % hydroxyethylcellulose solution and 1 mL of a 10 wt % aqueous solution of polyoxyethyleneoctyl phenyl ether, and the mixture was stirred with ultrasonic for one hour to prepare a titania paste, which is paste A. Separately, 3.0 g of titania microparticles were mixed with 7 mL of nitric acid at pH 0.7, and to the resulting mixture were added 0.2 mL of acetylacetone, 0.2 mL of a surfactant and polyethylene glycol having a molecular weight of 20,000, and the mixture was stirred with ultrasonic for one hour to prepare a titania paste, which is paste B. First, paste A was applied onto a transparent conductive glass electrode (from Asahi Glass Co., Ltd.) by a 100 μm doctor blade while masking a part of the electrode. Next, the resulting film was dried at room temperature, and then paste B was applied as described for paste A except using a 70 μm doctor blade to form a double-layered film. After drying, the film was calcined at 450° C. for 30 minutes to prepare a 1 cm$^2$ porous titania electrode (T-1).

Preparation of a Porous Titania Electrode (T-2)

A titania paste SP-100 from Showa Denko KK. was applied onto a transparent conductive glass electrode (from Asahi Glass Co., Ltd.) by a 200 μm doctor blade while masking a part of the electrode. The applied film was air-dried at room temperature for 5 minutes, and then calcined at 450° C. for 30 minutes to prepare a 1 cm$^2$ porous titania electrode (T-2).

Preparation of a Porous Titania Electrode (T-3)

3.0 g of titania microparticle was dispersed in 7 g of nitric acid at pH 0.7. To the paste was added 0.2 mL of acetylacetone and 0.2 mL of 10% Triton X as a surfactant. Next, to the mixture was added 1.2 g of polyethylene glycol having a molecular weight of 20,000 and finally 1 mL of ethanol, and then the paste was stirred and dispersed with ultrasonic for 15 minutes. This process of stirring with ultrasonic was repeated four times to prepare a paste. The resulting paste was applied onto a transparent conductive glass electrode (from Asahi Glass Co., Ltd.) by a 100 μm doctor blade while masking a part of the electrode. The resulting film was aged under the atmosphere of 25° C. and 60% for 10 minutes, and the aged film was calcined at 450° C. for 30 minutes. The cooled film was again subjected to the same process for forming a double-layered film to prepare a 1 cm$^2$ porous titania electrode (T-3).

2. Preparation of a Dye-Adsorbed Porous Titania Electrode

Preparation of D-1, D-2 or Comparative Dye A Adsorbed Porous Titania Electrodes

A porous titania electrode (T-1) was immersed in a saturated dye solution of each of D-1 and D-2 in ethanol/dimethyl sulfoxide (95:5) (less than 3×10$^{-4}$ mol/L) at 50° C. for 15 hours. Next, it was washed with ethanol and dried to give a dye-adsorbed porous titania electrode.

A Comparative dye A-adsorbed porous titania electrode was prepared as described above, except immersion in a 3×10$^{-4}$ mol/L ethanol solution at 50° C. for 4 hours.

Preparation of D-4, D-11, D-13, D-14 or Comparative Dye A Adsorbed Porous Titania Electrodes A porous titania electrode (T-2) was immersed in a saturated dye solution of each of D-4, D-11, D-13 and D-14 in t-butanol/acetonitrile (1:1) (less than $3\times10^{-4}$ mol/L) at 30° C. for 10 hours. Next, it was washed with acetonitrile and dried to give a dye-adsorbed porous titania electrode.

A Comparative dye A-adsorbed porous titania electrode was prepared as described above, except that a $3\times10^{-4}$ mol/L solution in t-butanol/acetonitrile (1:1) was used.

Preparation of D-4, D-5, D-6, D-7, D-8. D-9 or D-10 Adsorbed Porous Titania Electrodes A porous titania electrode (T-3) was immersed in a saturated dye solution of each of D-4, D-5, D-6, D-7, D-8, D-9 and D-10 in t-butanol/acetonitrile (1:1) (less than $3\times10^{-4}$ mol/L) at 30° C. for 20 hours. Next, it was washed with acetonitrile and dried to give a dye-adsorbed porous titania electrode.

3. Preparation of a Photochemical Battery

Figure 20:
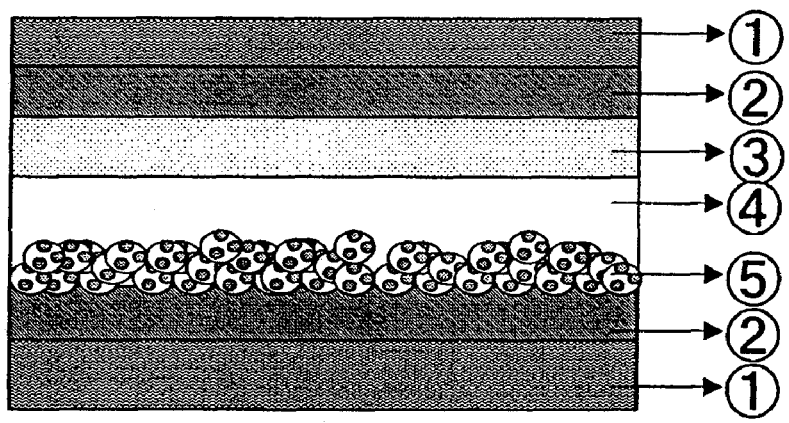
FIG. 20 is a cross-sectional view showing the configuration of the photochemical battery prepared according to the present invention.

A dye-adsorbed porous titania electrode thus obtained was combined with a platinum plate (counter electrode). Then, a solution of lithium iodide, iodine, 4-t-butylpyridine and 1,2-dimethyl-3-propylimidazolium iodide dissolved in 3-methoxypropionitrile to 0.1, 0.05, 0.5 and 0.6 mol/L, respectively as an electrolytic solution was infiltrated into a gap between these electrodes by capillary action to prepare a photochemical battery. FIG. 20 shows the structure of the photochemical battery prepared in this example.

4. Determination of Photoelectric Conversion Efficiency

The photoelectric conversion efficiency of the photochemical battery thus prepared was determined under irradiation with artificial solar light at 100 mW/cm$^2$ using a solar simulator (from EKO Instruments Co., Ltd.). Tables 1 and 2 summarize the photoelectric conversion efficiency for each dye. Table 3 shows the short-circuit current density per mol and the photoelectric conversion efficiency for D-4 and Comparative dye A.

TABLE 1

|  | Porous titania electrode | Photoelectric conversion efficiency (%) |
| --- | --- | --- |
| D-1 | T-1 | 1.8 |
| D-2 | T-1 | 2.6 |
| D-4 | T-2 | 4.6 |
| D-11 | T-2 | 4.4 |
| D-13 | T-2 | 3.7 |
| D-14 | T-2 | 2.8 |
| Comparative dye A | T-1 | 4.1 |
| Comparative dye A | T-2 | 4.3 |

TABLE 2

|  | Porous titania electrode | Photoelectric conversion efficiency (%) |
| --- | --- | --- |
| D-4 | T-3 | 5.4 |
| D-5 | T-3 | 4.9 |
| D-6 | T-3 | 3.3 |
| D-7 | T-3 | 4.4 |
| D-8 | T-3 | 4.2 |
| D-9 | T-3 | 4.7 |
| D-10 | T-3 | 4.3 |

TABLE 3

|  | Short-circuit current density ($\times10^8$ mA/mol·cm$^2$) | Photoelectric conversion efficiency ($\times10^7$%/mol) |
| --- | --- | --- |
| D-4 | 2.2 | 8.6 |
| Comparative dye A | 1.4 | 5.4 |

As seen from Table 1, metal complex dyes D-4 and D-11 of the present invention exhibit a higher photoelectric conversion efficiency than Comparative dye A. As seen from Table 2, the complexes of the present invention which is the same as metal complex dye D-4 except a counter anion (D-5, D-6, D-7, D-8, D-9 and D-10) exhibit a high photoelectric conversion efficiency. As seen from Table 3, the metal complex dye of the present invention has an improved short-circuit current density per molecule and an improved photoelectric conversion efficiency in comparison with Comparative dye A, which demonstrate that the metal complex dye of the present invention has an improved photoelectric conversion ability.

Example 13

Evaluation of Dyes for Thermal Stability

D-4, D-11, D-13 and Comparative dye A were evaluated for their thermal stability from a temperature of generation of a decomposition gas component under an artificial air (He: 80%+$O_2$: 20%) by TG-MS analysis. TG analysis was conducted using Thermo plus TG8120 (from Rigaku Corporation) under the conditions of a temperature increase rate: 10° C./min and an artificial-air flow rate: 100 mL/min, and injection into an MS apparatus carried out at a transfer-line temperature of 200° C. MS spectra were obtained using a mass spectrometer QP-5000 complex system (from Shimadzu Corporation) under the conditions of an inlet temperature: 250° C., an interface temperature: 300° C., an ionization method: EI (70 eV) and a mass scanning range: 10 to 300.

Table 4 shows an initiation temperature of generation of a gas component derived from a ligand which generates when each dye is thermally decomposed.

TABLE 4

|  | Gas component | Initiation temperature of gas generation (° C.) |
| --- | --- | --- |
| D-4 | $CO_2$ | 280 |
| D-11 | $CO_2$ | 300 |
| D-13 | $CO_2$ | 280 |
| Comparative dye A | $CO_2$ | 250 |
| Comparative dye A | $SO_2$ | 240 |

As seen from Table 4, an initiation temperature of generation of $CO_2$ which is considered to be a gas component derived from a carboxyl group (—COOH) is higher by 30° C. in any of the binuclear metal complexes of the present invention compared with Comparative dye A. Furthermore, generation of $SO_2$ which is considered to be a gas component derived from an isothiocyanato group (—NCS) was observed at a temperature lower than a decomposition temperature of a carboxyl group for Comparative dye A, while no other gas components were observed in a temperature range lower than the decomposition temperature of a carboxyl group for the binuclear metal complexes of the present invention. A binuclear metal complex of the present invention is, therefore, very preferable because of its high thermal stability due to less decomposable sites.

Example 14

Preparation of a Dye-Adsorbed Porous Titania Electrode

A porous titania electrode in which the binuclear metal complex dye (D-4) of the present invention obtained in Example 4 was adsorbed was prepared. The procedure will be described below.

Preparation of a Porous Titania Electrode

To 5.0004 g of a 30 wt % titania microparticle dispersed slurry (Titan Kogyo KK., 20 nm microparticles) were added 0.2 mL of acetylacetone, 1 mL of a 2 wt % hydroxyethylcellulose and 1 mL of a 10 wt % aqueous solution of polyoxyethyleneoctyl phenyl ether, and the mixture was stirred with ultrasonic for one hour to prepare a titania paste, which was paste A. Separately, 2.9997 g of titania microparticles were mixed with 7 mL of nitric acid at pH 0.7, and to the resulting mixture were added 0.2 mL of acetylacetone, 0.2 mL of a surfactant and polyethylene glycol having a molecular weight of 20,000, and the mixture was stirred with ultrasonic for one hour to prepare a titania paste, which was paste B. Paste A was applied onto a transparent conductive glass electrode by a doctor blade using a 50 μm spacer to prepare a film. After drying the film at room temperature, paste B was applied to the film in a similar way, which was dried and calcined at 450° C. for 30 minutes to prepare 1 cm² and 5 cm² porous titania electrodes.

Next, a saturated solution of the binuclear metal complex dye of the present invention (D-4) obtained in Example 4 in ethanol (3×10⁻⁴ mol/L or less) was prepared as a dye solution, in which was then immersed the electrodes at 50° C. for 15 hours. After the immersion, they were washed with ethanol and dried under a nitrogen stream to give 1 cm² and 5 Cm² dye-adsorbed porous titania electrodes.

Comparative Example 1

1 cm² and 5 cm² dye-adsorbed porous titania electrodes were prepared as described in Example 14, except using a 3×10⁻⁴ mol/L dye solution of Comparative dye A represented by the above formula (A) in ethanol as a dye.

Example 15

Determination of the Amount of Dye Adsorption

The amount of an adsorbed dye was determined for each of 5 cm² dye-adsorbed porous titania electrodes obtained in Example 14 and Comparative Example 1. The procedure will be described below.

A dye was desorbed by immersing a dye-adsorbed porous titania electrode in a 0.01 mol/L solution of sodium hydroxide in ethanol/water (1:1) overnight. The amount of dye adsorption per 1 cm² was calculated from an absorption spectrum of the resulting desorption solution (by JASCO Corporation, V-570). Table 5 summarizes the results on an adsorption amount for each of the binuclear metal complex dye (D-4) obtained in Example 4 and Comparative dye A.

TABLE 5

| Metal complex dye | Dye-adsorption amount ($10^{-8}$ mol/cm²) |
|---|---|
| D-4 | 6.5 |
| Comparative dye A | 8.8 |

Example 16

Preparation of a Photochemical Battery

There will be described a procedure for preparing a photochemical battery.

A 1 Cm² dye-adsorbed porous titania electrode prepared in Example 14 or Comparative Example 1 was combined with a platinum plate (counter electrode). Then, a solution of lithium iodide, iodine, 4-t-butylpyridine and 1,2-dimethyl-3-propylimidazolium iodide dissolved in 3-methoxypropionitrile to 0.1, 0.05, 0.5 and 0.6 mol/L, respectively as an electrolytic solution was infiltrated into a gap between these electrodes by capillary action to prepare a photochemical battery.

Example 17

Evaluation of a Photochemical Battery

A photochemical battery was evaluated by irradiating the photochemical battery obtained in Example 16 with artificial solar light at 100 mW/cm² using a solar simulator (from EKO Instruments Co., Ltd.). Table 6 summarizes the property values for each of the binuclear metal complex dye of the present invention (D-4) obtained in Example 4 and Comparative dye A. Jsc and Voc in Table 6 represent a short-circuit current density per 1 mol of a metal complex dye and an open voltage, respectively. The short-circuit current densities per 1 mol of dye were calculated from the results in Table 5.

TABLE 6

| Metal complex dye | Jsc ($10^5$ A·mol⁻¹·cm⁻²) | Voc (V) |
|---|---|---|
| D-4 | 1.72 | 0.71 |
| Comparative dye A | 1.49 | 0.66 |

As seen from Table 6, a short-circuit current density per molecule is higher in the binuclear metal complex dye of the present invention (D-4) obtained in Example 4 compared with Comparative dye A, which demonstrate unambiguously that the binuclear metal complex dye of the present invention has an improved photoelectric conversion ability.

Example 18

Synthesis of a Binuclear Metal Complex

[(Hdcbpy)₂Ru(bpm)Ru(bpy)₂](PF₆)₂ (D-16)

1. Synthesis of a Mononuclear Metal Complex [(bpm)Ru(bpy)₂](PF₆)₂ (M²C-8)

Under nitrogen atmosphere, in a 100 mL three-necked flask were placed Ru(bpy)₂Cl₂ (0.216 g, 0.42 mmol) prepared in Example 1, 2,2'-bipyrimidine (bpm) (0.133 g, 0.84 mmol) and 40 mL of ethanol/water (1:1), and the mixture was refluxed under irradiation with 2.45 GHz microwave for 30 minutes. After the mixture cooled down, an aqueous solution of NH$_4$PF$_6$ was added to precipitate a complex as a salt of counter anion PF$_6^-$. The precipitate was collected by filtration, and then washed with water and recrystallized from acetone/diethyl ether. After collecting the precipitated crystals by filtration, they were washed with diethyl ether. After drying under vacuum, 0.259 g of M$^2$C-8 was obtained (yield: 71%).

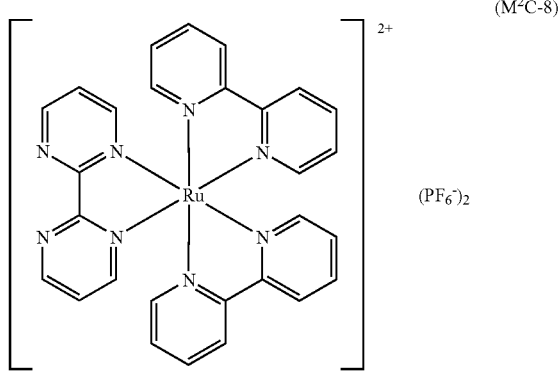

(M$^2$C-8)

2. Synthesis of D-16

Under nitrogen atmosphere, in a 100 mL three-necked flask were placed M$^1$C-1 (0.102 g, 0.15 mmol) and 40 mL of ethanol/water (1:1), and 0.6 mL of a 1 mol/L sodium hydroxide solution was added dropwise to give a solution. To the solution was added M$^2$C-8 (0.135 g, 0.15 mmol), and the mixture was refluxed under irradiation with 2.45 GHz microwave for 10 minutes. After cooling down, the mixture was filtered, and ethanol in the resulting filtrate was evaporated under vacuum to dryness. The resulting suspension was filtered, and to the filtrate was added dropwise a 0.5 mol/L aqueous hexafluorophosphoric acid solution to pH 2.5. The precipitated complex was collected by filtration, and washed with an aqueous hexafluorophosphoric acid solution at pH 2.5, acetone/diethyl ether (4:1) and diethyl ether. After drying under vacuum, 0.108 g of D-16 was obtained (yield: 42%). The elemental analysis results were in good agreement with the values of a tetrahydrate.

Elemental Analysis
Observed: C:41.30, H:3.40, N:10.90
Calculated: C:41.06, H:2.92, N:11.05.
$^1$H-NMR spectrum of the complex is shown in FIG. 21.

Example 19

Quantum Chemical Calculation for a Binuclear Metal Complex Dye

A binuclear metal complex model was structurally optimized by quantum chemical calculation. The software used was Material Studio 2.0. A calculation method was a density functional theory (DFT), where an exchange correlation function was VWN and a basis function system was DNP. For simplifying calculation, an effective core potential approximation was used. (In the structural optimization, a convergence condition to energy was 10$^{-5}$ a.u. or less. In terms of SCF performed in the structural optimization calculation, a convergence condition to energy was 10$^{-6}$ a.u. or less.)

For the complex model obtained from the above structural optimization, an energy state was calculated by quantum chemical calculation. A calculation method was a density functional theory. And a specific exchange correlation function was BLYP. A basis function system was DNP. Furthermore, for simplifying calculation, an effective core potential approximation was used. (In terms of SCF calculation, a convergence condition to energy was 10$^{-6}$ a.u. or less, and the condition was imposed that an electron occupation number for each state was an integer from 0 to 2 both inclusive.)

For the above results, FIG. 22 shows a visualized shape of a HOMO (including a next HOMO) orbital in the structure shown in the binuclear metal complex dye of the present invention (D-4) prepared in Example 4; FIG. 23 shows a visualized shape of a LUMO (including a next LUMO) orbital in the structure shown in the binuclear metal complex dye (D-4); FIG. 24 shows a visualized shape of a HOMO (including a next HOMO) orbital in the structure shown in the binuclear metal complex dye (D-16) prepared in Example 18; and FIG. 25 shows a visualized shape of a LUMO (including a next LUMO) orbital in the structure shown in the binuclear metal complex dye (D-16). The visualization was performed under the conditions of Iso-Value=±0.03 using the software, Material Studio 2.0. FIG. 26 conceptually shows an electron-transition direction in HOMO-LUMO in an asymmetric binuclear metal complex represented by the general formula: (L$^1$)$_2$M$^1$(BL)M$^2$(L$^2$)$_2$(X)$_n$ wherein L$^1$, M$^1$, BL, M$^2$, L$^2$ and X are as defined above; and electron flow within a photochemical battery circuit. In FIG. 26, X is omitted.

As shown in FIG. 26, a HOMO and a LUMO preferably have such an orbital configuration that a direction of electron transition in HOMO-LUMO is identical to a direction of electron flow within a photochemical battery circuit. As seen from FIGS. 22 and 23, these two directions are identical in the binuclear metal complex dye (D-4) of the present invention; while as seen from FIGS. 24 and 25, these two directions are not identical in the binuclear metal complex dye (D-16) prepared in Example 18. It can be, therefore, understood that the binuclear metal complex dye (D-4) of the present invention allows smoother electron transfer, thereby obtaining an efficient photochemical battery.

Comparative Example 2

For the binuclear metal complex dye (D-16) prepared in Example 18, a photochemical battery was prepared and the photoelectric conversion efficiency was determined as described in Example 12, except substituting a saturated solution of a dye in ethanol for a saturated solution of a dye in ethanol/dimethyl sulfoxide (95:5) in the preparation of D-1, D-2 or Comparative dye A adsorbed porous titania electrodes. Table 7 shows the results on a photoelectric conversion efficiency and FIG. 27 shows a current-voltage characteristic curve. A photoelectric conversion efficiency and a current-voltage characteristic curve for D-4 obtained in Example 12 are also shown in Table 7 and FIG. 27, respectively.

TABLE 7

| | Photoelectric conversion efficiency (%) |
|---|---|
| D-4 | 4.6 |
| D-16 | <0.1 |

Table 7, FIG. 27 and the results of Example 19 show that the binuclear metal complex dye (D-4) of the present invention with a proper HOMO-LUMO orbital configuration is significantly improved in photochemical battery properties as compared with the binuclear metal complex dye (D-16) prepared in Example 18 with an improper HOMO-LUMO orbital configuration.

Comparative Example 3

For the binuclear metal complex dye (D-16) prepared in Example 18, a photochemical battery was evaluated as described in Example 17, after preparing a 1 cm² dye-adsorbed porous titania electrode as described in Example 14 and preparing a photochemical battery as described in Example 16. Table 8 shows the results on a photoelectric conversion efficiency (η) and FIG. 28 shows a current-voltage characteristic curve. The results on a photoelectric conversion efficiency (η) and a current-voltage characteristic curve for the binuclear metal complex dye (D-4) of the present invention prepared in Example 17 are also shown in Table 8 and FIG. 28, respectively.

TABLE 8

| Metal complex dye | η (%) |
| --- | --- |
| D-4 | 4.0 |
| D-16 | <0.1 |

Table 8, FIG. 28 and the results of Example 19 show that the binuclear metal complex dye (D-4) of the present invention prepared in Example 4 with a proper HOMO-LUMO orbital configuration is significantly improved in photochemical battery properties as compared with the binuclear metal complex dye (D-16) prepared in Example 18 with an improper HOMO-LUMO orbital configuration.

The invention claimed is:

1. An asymmetric binuclear metal complex represented by the general formula: $(L^1)_2 M^1(BL)M^2(L^2)_2(X)_n$ wherein $M^1$ and $M^2$, which may be identical or different, represent ruthenium (Ru), osmium (Os), cobalt (Co), nickel (Ni), copper (Cu) or iron (Fe);

$L^1$ represents a ligand represented by the formula ($L^1$-A):

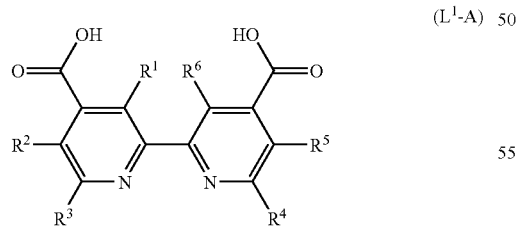

wherein H in —COOH may be liberated; and $R^1$, $R^2$, $R^3$, $R^4$, $R^5$ and $R^6$ independently represent hydrogen, alkyl containing 1 to 6 carbon atoms, or alkoxy containing 1 to 6 carbon atoms, or alternatively, $R^2$ and $R^3$, $R^4$ and $R^5$, or $R^1$ and $R^6$ may form a substituted or unsubstituted six-membered aromatic hydrocarbon ring together with the carbon atoms to which they are bound;

$L^2$ represents a ligand represented by the formula ($L^2$-A):

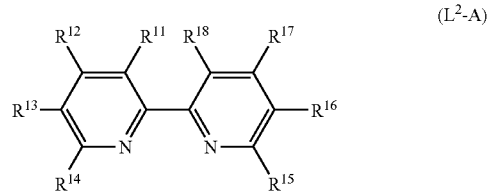

wherein $R^{11}$, $R_{12}$, $R^{13}$, $R^{14}$, $R^{15}$, $R^{16}$, $R^{17}$ and $R^{18}$ independently represent hydrogen, alkyl containing 1 to 6 carbon atoms, or alkoxy containing 1 to 6 carbon atoms, or alternatively, adjacent two of $R^{11}$ to $R^{18}$ or $R^{11}$ to $R^{18}$ may form a substituted or unsubstituted six-membered aromatic hydrocarbon ring together with the carbon atoms to which they are bound;

and two $L^1$s may be different and two $L^2$s may be different;

BL represents a bridge ligand represented by the formula (BL-C):

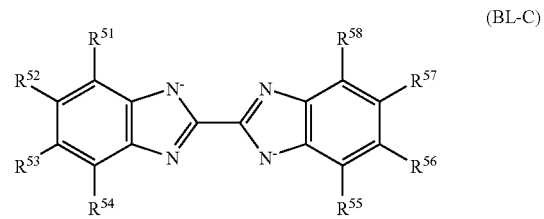

wherein $R^{51}$, $R^{52}$, $R^{53}$ and $R^{54}$ independently represent hydrogen, alkyl containing 1 to 6 carbon atoms, or alkoxy containing 1 to 6 carbon atoms, or alternatively, adjacent two of $R^{51}$ to $R^{54}$ may form a substituted or unsubstituted six-membered aromatic hydrocarbon ring together with the carbon atoms to which they are bound; and $R^{55}$, $R^{56}$, $R^{57}$ and $R^{58}$ independently represent hydrogen, alkyl containing 1 to 6 carbon atoms, or alkoxy containing 1 to 6 carbon atoms, or alternatively, adjacent two of $R^{55}$ to $R^{58}$ may form a substituted or unsubstituted six-membered aromatic hydrocarbon ring together with the carbon atoms to which they are bound, the heteroatoms contained in the cyclic structures being ligand atoms coordinating to $M^1$ and $M^2$;

X represents a counter ion; and n is the number of counter ions needed to neutralize the charge of the complex.

2. The binuclear metal complex as claimed in claim 1, wherein $L^1$ is a ligand represented by the formula ($L^1$-1) or ($L^1$-4):

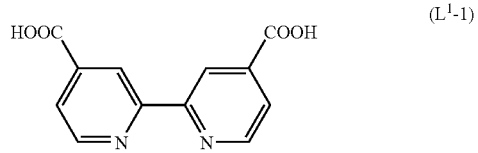

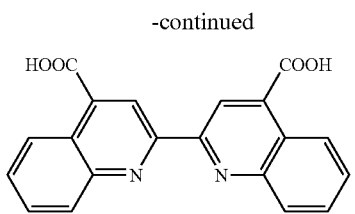

wherein the heterocyclic ring may be substituted; and H in —COOH may be liberated.

3. The binuclear metal complex as claimed in claim 1, wherein $L^2$ is a ligand represented by any of the formulas (L²-1), (L²-2) and (L²-4):

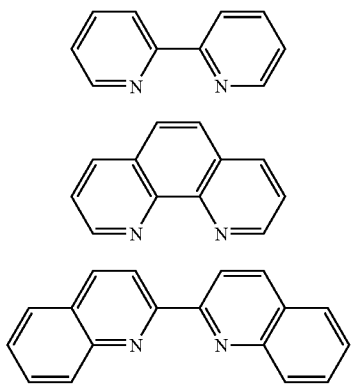

wherein the heterocyclic ring and the benzene ring may be substituted.

4. The binuclear metal complex as claimed in claim 1, wherein BL is a ligand represented by the formula (BL-4):

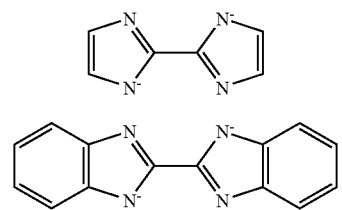

wherein the heterocyclic ring and the benzene ring may be substituted.

5. The binuclear metal complex as claimed in claim 1, wherein $L^1$ is a ligand represented by the above formula (L¹-1) or (L¹-4);

$L^2$ is a ligand represented by any of the above formulas (L²-1), (L²-2) and (L²-4);

BL is a ligand represented by formula (BL-4)

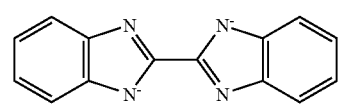

and $M^1$ and $M^2$ are independently selected from the group consisting of ruthenium (Ru), osmium (Os), cobalt (Co), nickel (Ni), copper (Cu) and iron (Fe).

6. A semiconductor-sensitizing dye comprising an asymmetric binuclear metal complex represented by the general formula: $(L^1)_2M^1(BL)M^2(L^2)_2(X)_n$, wherein $M^1$ and $M^2$, which may be identical or different, represent ruthenium (RU), osmium (Os), cobalt (Co), nickel (Ni), copper (Cu) or iron (Fe);

$L^1$ represents a ligand represented by the formula (L¹-A):

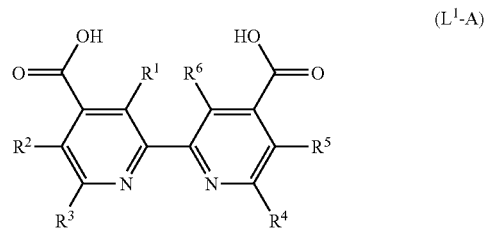

wherein H in —COOH may be liberated; and $R^1$, $R^2$, $R^3$, $R^4$, $R^5$ and $R^6$ independently represent hydrogen, alkyl containing 1 to 6 carbon atoms, or alkoxy containing 1 to 6 carbon atoms, or alternatively, $R^2$ and $R^3$, $R^4$ and $R^5$, or $R^1$ and $R^6$ may form a substituted or unsubstituted six-membered aromatic hydrocarbon ring together with the carbon atoms to which they are bound;

$L^2$ represents a ligand represented by the formula (L²-A):

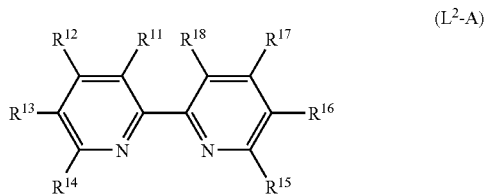

wherein $R^{11}$, $R^{12}$, $R^{13}$, $R^{14}$, $R^{15}$, $R^{16}$, $R^{17}$ and $R^{18}$ independently represent hydrogen, alkyl containing 1 to 6 carbon atoms, or alkoxy containing 1 to 6 carbon atoms, or alternatively, adjacent two of $R^{11}$ to $R^{18}$ or $R^{11}$ to $R^{18}$ may form a substituted or unsubstituted six-membered aromatic hydrocarbon ring together with the carbon atoms to which they are bound;

and two $L^1$s may be different and two $L^2$s may be different;

X represents a counter ion;

n is the number of counter ions needed to neutralize the charge of the complex;

BL represents a bridge ligand represented by the formula (BL-C):

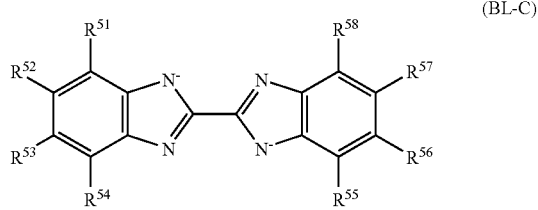

wherein $R^{51}$, $R^{52}$, $R^{53}$ and $R^{54}$ independently represent hydrogen, alkyl containing 1 to 6 carbon atoms, or alkoxy containing 1 to 6 carbon atoms, or alternatively, adjacent two of $R^{51}$ to $R^{54}$ may form a substituted or unsubstituted six-membered aromatic hydrocarbon ring together with the carbon atoms to which they are bound; and $R^{55}$, $R^{56}$, $R^{57}$ and $R^{58}$ independently represent hydrogen, alkyl containing 1 to 6 carbon atoms, or alkoxy containing 1 to 6 carbon atoms, or alternatively, adjacent two of $R^{55}$ to $R^{58}$ may form a substituted or unsubstituted six-membered aromatic hydrocarbon ring together with the carbon atoms to which they are bound, the heteroatoms contained in the cyclic structures being ligand atoms coordinating to $M^1$ and $M^2$.

7. The semiconductor-sensitizing dye as claimed in claim 6, wherein $L^1$ is a ligand represented by the above formula ($L^1$-1);

$L^2$ is a ligand represented by the above formula ($L^2$-1) or ($L^2$-2);

BL is a ligand represented by formula (BL-4)

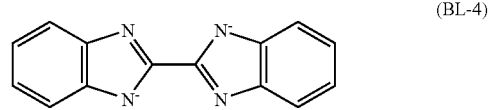

(BL-4)

and $M^1$ and $M^2$ are independently selected from the group consisting of ruthenium (Ru), osmium (Os), cobalt (Co), nickel (Ni), copper (Cu) and iron (Fe).

8. The semiconductor-sensitizing dye as claimed in claim 6, wherein LUMOs are predominantly distributed in $(L^1)_2 M^1$.

* * * * *

UNITED STATES PATENT AND TRADEMARK OFFICE
CERTIFICATE OF CORRECTION

PATENT NO. : 7,825,250 B2  
APPLICATION NO. : 11/575745  
DATED : November 2, 2010  
INVENTOR(S) : Yoshihisa Kakuta et al.

Page 1 of 1

It is certified that error appears in the above-identified patent and that said Letters Patent is hereby corrected as shown below:

At Column 40, Line 16, in Claim 1, change "or $R^{11}$ to $R^{18}$" to --or $R^{11}$ and $R^{18}$--;

At Column 42, Line 46, in Claim 6, change "or $R^{11}$ to $R^{18}$" to --or $R^{11}$ and $R^{18}$--.

Signed and Sealed this
Thirteenth Day of September, 2011

David J. Kappos
*Director of the United States Patent and Trademark Office*